US006653447B1

(12) United States Patent
Cosman et al.

(10) Patent No.: US 6,653,447 B1
(45) Date of Patent: Nov. 25, 2003

(54) ULBP DNA AND POLYPEPTIDES

(75) Inventors: David J. Cosman, Bainbridge Island, WA (US); Jurgen Mullberg, Aachen (DE); William C. Fanslow, III, Normandy Park, WA (US); Marek Kubin, Bainbridge Island, WA (US); Richard Jeffrey Armitage, Bainbridge Island, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/524,100

(22) Filed: Mar. 13, 2000

Related U.S. Application Data

(63) Continuation-in-part of application No. PCT/US98/27048, filed on Dec. 17, 1998.
(60) Provisional application No. 60/069,857, filed on Dec. 17, 1997, and provisional application No. 60/092,946, filed on Jul. 15, 1998.

(51) Int. Cl.[7] .................................................. C07K 1/00
(52) U.S. Cl. ................... 530/350; 435/69.1; 435/320.1; 530/300; 536/23.1
(58) Field of Search ............................ 435/69.1, 320.1; 514/44; 530/300, 350; 536/23.1

(56) References Cited

PUBLICATIONS

Dorfman, D. et al., "In vivo expression of B7–1 and B7–2 by follicular lymphoma cells can prevent induction of T–cell anergy but is insufficient to induce significant T–cell proliferation," *Blood* 90(11): 4297–4306, (Dec. 1, 1997).
Gattei, V. et al., "CD30 ligand is frequently expressed in human hematopoietic malignancies of myeloid and lymphoid origin," *Blood* 89(6): 2048–2059, (Mar. 15, 1997).
Myers, D. and Uckun, F., "An anti–CD72 immunotoxin against therapy–refractory B–lineage acute lymphoblastic leukemia," *Leukemia and Lymphoma*18:119–122, Harwood Academic Publishecs GmbH, Printed in Singapore, (1995).
Sun, T. et al., "Histiocyte–rich B–cell lymphoma," *Human Pathology* 28(11): 1321–1324. (11/97).
Whiteside, T. and Herberman, R., "The role of natural killer cells in immune surveillance of cancer," *Current Opinion in Immunology* 7:704–710, (1995).
GenBank Accession No. AI091180 (1997).
GenBank Accession No. R25716 (1995).

*Primary Examiner*—James Housel
*Assistant Examiner*—Ulrike Winkler
(74) *Attorney, Agent, or Firm*—Rosemary Sweeney; Janis C. Henry; Stuart Watt

(57) ABSTRACT

The invention is directed to purified and isolated novel ULBP polypeptides, the nucleic acids encoding such polypeptides, processes for production of recombinant forms of such polypeptides, antibodies generated against these polypeptides, fragmented peptides derived from these polypeptides, and the uses of the above. ULBP polypeptide can be found on the surface of human B cell lymphomas. Mammalian forms of ULBP polypeptide in isolated or purified forms are provided. In addition, isolated nucleic acids encoding ULBP polypeptides and expression vectors comprising a cDNA encoding ULBP polypeptides are provided. The ULBP polypeptides can be isolated or synthesized and used to prepare antibodies, and in particular monoclonal antibodies, against the polypeptides. The antibodies, in turn, are useful for detecting the presence of ULBP polypeptides in human cell samples, which can be correlated with the existence of a malignant condition in a patient. ULBP polypeptides stimulate IFN-γ production, NK cell proliferation, and CTL activity.

32 Claims, No Drawings

SEQUENCE LISTING

<160> NUMBER OF SEQ ID NOS: 14

<210> SEQ ID NO 1
<211> LENGTH: 735
<212> TYPE: DNA
<213> ORGANISM: Homo sapiens

<400> SEQUENCE: 1

```
atggcagcgg ccgccagccc cgccttcctt ctgtgcctcc cgcttctgca cctgctgtct      60
ggctggtccc gggcaggatg ggtcgacaca cactgtcttt gctatgactt catcatcact     120
cctaagtcca gacctgaacc acagtggtgt gaagttcaag gcctggtgga tgaaaggcct     180
tttcttcact atgactgtgt taaccacaag gccaaagcct ttgcttctct ggggaagaaa     240
gtcaatgtca caaaaacctg ggaagaacaa actgaaacac taagagacgt ggtggatttc     300
cttaaagggc aactgcttga cattcaagtg gagaatttaa tacccattga gccctcacc     360 ctgcaggcca ggatgtcttg tgagcatgaa gcccatggac acggcagagg atcttggcag     420
ttcctcttca atggacagaa gttcctcctc tttgactcaa acaacagaaa gtggacagca     480
cttcatcctg gagccaagaa gatgacagag aagtgggaga agaacaggga tgtgaccatg     540
ttcttccaga agatttcact gggggattgt aagatgtggc ttgaagaatt tttgatgtac     600
tgggaacaaa tgctggatcc aacaaaacca ccctctctgg ccccaggcac aacccaaccc     660
aaggccatgg ccaccaccct cagtccctgg agccttctca tcatcttcct ctgcttcatt     720
```
ctagctggca gatga 735

<210> SEQ ID NO 2
<211> LENGTH: 244
<212> TYPE: PRT
<213> ORGANISM: Homo sapiens

<400> SEQUENCE: 2

```
Met Ala Ala Ala Ser Pro Ala Phe Leu Cys Leu Pro Leu Leu
1               5                   10                  15

His Leu Leu Ser Gly Trp Ser Arg Ala Gly Trp Val Asp Thr His Cys
            20                  25                  30

Leu Cys Tyr Asp Phe Ile Ile Thr Pro Lys Ser Arg Pro Glu Pro Gln
            35                  40                  45

Trp Cys Glu Val Gln Gly Leu Val Asp Glu Arg Pro Phe Leu His Tyr
    50                  55                  60

Asp Cys Val Asn His Lys Ala Lys Ala Phe Ala Ser Leu Gly Lys Lys
65                  70                  75                  80

Val Asn Val Thr Lys Thr Trp Glu Glu Gln Thr Glu Thr Leu Arg Asp
                85                  90                  95

Val Val Asp Phe Leu Lys Gly Gln Leu Leu Asp Ile Gln Val Glu Asn
            100                 105                 110

Leu Ile Pro Ile Glu Pro Leu Thr Leu Gln Ala Arg Met Ser Cys Glu
        115                 120                 125

His Glu Ala His Gly His Gly Arg Gly Ser Trp Gln Phe Leu Phe Asn
    130                 135                 140

Gly Gln Lys Phe Leu Leu Phe Asp Ser Asn Asn Arg Lys Trp Thr Ala
145                 150                 155                 160

Leu His Pro Gly Ala Lys Lys Met Thr Glu Lys Trp Glu Lys Asn Arg
                165                 170                 175

Asp Val Thr Met Phe Phe Gln Lys Ile Ser Leu Gly Asp Cys Lys Met
            180                 185                 190

Trp Leu Glu Glu Phe Leu Met Tyr Trp Glu Gln Met Leu Asp Pro Thr
        195                 200                 205

Lys Pro Pro Ser Leu Ala Pro Gly Thr Thr Gln Pro Lys Ala Met Ala
    210                 215                 220

Thr Thr Leu Ser Pro Trp Ser Leu Leu Ile Ile Phe Leu Cys Phe Ile
225                 230                 235                 240

Leu Ala Gly Arg
```

<210> SEQ ID NO 3
<211> LENGTH: 741
<212> TYPE: DNA
<213> ORGANISM: Homo sapiens

<400> SEQUENCE: 3
atggcagcag ccgccgctac caagatcctt ctgtgcctcc cgcttctgct cctgctgtcc      60
ggctggtccc gggctgggcg agccgaccct cactctcttt gctatgacat caccgtcatc     120
cctaagttca gacctggacc acggtggtgt gcggttcaag gccaggtgga tgaaaagact     180
tttcttcact atgactgtgg caacaagaca gtcacacctg tcagtcccct ggggaagaaa     240
ctaaatgtca aacggcctg aaagcacag aacccagtac tgagagaggt ggtggacata     300
cttacagagc aactgcgtga cattcagctg gagaattaca cacccaagga acccctcacc     360
ctgcaggcaa ggatgtcttg tgagcagaaa gctgaaggac acagcagtgg atcttggcag     420

```
ttcagtttcg atgggcagat cttcctcctc tttgactcag agaagagaat gtggacaacg      480
gttcatcctg gagccagaaa gatgaaagaa aagtgggaga atgacaaggt tgtggccatg      540
tccttccatt acttctcaat gggagactgt ataggatggc ttgaggactt cttgatgggc      600
atggacagca ccctggagcc aagtgcagga gcaccactcg ccatgtcctc aggcacaacc      660
caactcaggg ccacagccac caccctcatc ctttgctgcc tcctcatcat cctcccctgc      720
ttcatcctcc ctggcatctg a                                                741
```

<210> SEQ ID NO 4
<211> LENGTH: 246
<212> TYPE: PRT
<213> ORGANISM: Homo sapiens

<400> SEQUENCE: 4

```
Met Ala Ala Ala Ala Thr Lys Ile Leu Leu Cys Leu Pro Leu Leu
 1               5                  10                  15

Leu Leu Leu Ser Gly Trp Ser Arg Ala Gly Arg Ala Asp Pro His Ser
            20                  25                  30

Leu Cys Tyr Asp Ile Thr Val Ile Pro Lys Phe Arg Pro Gly Pro Arg
        35                  40                  45

Trp Cys Ala Val Gln Gly Gln Val Asp Glu Lys Thr Phe Leu His Tyr
    50                  55                  60

Asp Cys Gly Asn Lys Thr Val Thr Pro Val Ser Pro Leu Gly Lys Lys
65                  70                  75                  80

Leu Asn Val Thr Thr Ala Trp Lys Ala Gln Asn Pro Val Leu Arg Glu
                85                  90                  95

Val Val Asp Ile Leu Thr Glu Gln Leu Arg Asp Ile Gln Leu Glu Asn
            100                 105                 110

Tyr Thr Pro Lys Glu Pro Leu Thr Leu Gln Ala Arg Met Ser Cys Glu
        115                 120                 125

Gln Lys Ala Glu Gly His Ser Ser Gly Ser Trp Gln Phe Ser Phe Asp
    130                 135                 140

Gly Gln Ile Phe Leu Leu Phe Asp Ser Glu Lys Arg Met Trp Thr Thr
145                 150                 155                 160

Val His Pro Gly Ala Arg Lys Met Lys Glu Lys Trp Glu Asn Asp Lys
                165                 170                 175

Val Val Ala Met Ser Phe His Tyr Phe Ser Met Gly Asp Cys Ile Gly
            180                 185                 190

Trp Leu Glu Asp Phe Leu Met Gly Met Asp Ser Thr Leu Glu Pro Ser
        195                 200                 205

Ala Gly Ala Pro Leu Ala Met Ser Ser Gly Thr Thr Gln Leu Arg Ala
    210                 215                 220

Thr Ala Thr Thr Leu Ile Leu Cys Cys Leu Leu Ile Ile Leu Pro Cys
225                 230                 235                 240

Phe Ile Leu Pro Gly Ile
                245
```

<210> SEQ ID NO 5
<211> LENGTH: 450
<212> TYPE: PRT
<213> ORGANISM: Artificial Sequence
<220> FEATURE:
<223> OTHER INFORMATION: Peptides
<220> FEATURE:
<221> NAME/KEY: PEPTIDE
<222> LOCATION: (1)..(219)
<223> OTHER INFORMATION: ULBP-1 sequences -continued

```
<220> FEATURE:
<221> NAME/KEY: PEPTIDE
<222> LOCATION: (220)..(450)
<223> OTHER INFORMATION: Human Ig Fc sequences

<400> SEQUENCE: 5
```

| Met | Ala | Ala | Ala | Ser | Pro | Ala | Phe | Leu | Leu | Cys | Leu | Pro | Leu | Leu |
|---|---|---|---|---|---|---|---|---|---|---|---|---|---|---|
| 1 | | | | 5 | | | | | 10 | | | | | 15 |

| His | Leu | Leu | Ser | Gly | Trp | Ser | Arg | Ala | Gly | Trp | Val | Asp | Thr | His | Cys |
|---|---|---|---|---|---|---|---|---|---|---|---|---|---|---|---|
| | | | 20 | | | | | 25 | | | | | 30 | | |

| Leu | Cys | Tyr | Asp | Phe | Ile | Ile | Thr | Pro | Lys | Ser | Arg | Pro | Glu | Pro | Gln |
|---|---|---|---|---|---|---|---|---|---|---|---|---|---|---|---|
| | | 35 | | | | 40 | | | | | 45 | | | | |

| Trp | Cys | Glu | Val | Gln | Gly | Leu | Val | Asp | Glu | Arg | Pro | Phe | Leu | His | Tyr |
|---|---|---|---|---|---|---|---|---|---|---|---|---|---|---|---|
| | 50 | | | | | 55 | | | | | 60 | | | | |

| Asp | Cys | Val | Asn | His | Lys | Ala | Lys | Ala | Phe | Ala | Ser | Leu | Gly | Lys | Lys |
|---|---|---|---|---|---|---|---|---|---|---|---|---|---|---|---|
| 65 | | | | | 70 | | | | | 75 | | | | | 80 |

| Val | Asn | Val | Thr | Lys | Thr | Trp | Glu | Glu | Gln | Thr | Glu | Thr | Leu | Arg | Asp |
|---|---|---|---|---|---|---|---|---|---|---|---|---|---|---|---|
| | | | | 85 | | | | | 90 | | | | | 95 | |

| Val | Val | Asp | Phe | Leu | Lys | Gly | Gln | Leu | Leu | Asp | Ile | Gln | Val | Glu | Asn |
|---|---|---|---|---|---|---|---|---|---|---|---|---|---|---|---|
| | | | | 100 | | | | | 105 | | | | | 110 | |

| Leu | Ile | Pro | Ile | Glu | Pro | Leu | Thr | Leu | Gln | Ala | Arg | Met | Ser | Cys | Glu |
|---|---|---|---|---|---|---|---|---|---|---|---|---|---|---|---|
| | | 115 | | | | | 120 | | | | | 125 | | | |

| His | Glu | Ala | His | Gly | His | Gly | Arg | Gly | Ser | Trp | Gln | Phe | Leu | Phe | Asn |
|---|---|---|---|---|---|---|---|---|---|---|---|---|---|---|---|
| | 130 | | | | | 135 | | | | | 140 | | | | |

| Gly | Gln | Lys | Phe | Leu | Leu | Phe | Asp | Ser | Asn | Asn | Arg | Lys | Trp | Thr | Ala |
|---|---|---|---|---|---|---|---|---|---|---|---|---|---|---|---|
| 145 | | | | | 150 | | | | | 155 | | | | | 160 |

| Leu | His | Pro | Gly | Ala | Lys | Lys | Met | Thr | Glu | Lys | Trp | Glu | Lys | Asn | Arg |
|---|---|---|---|---|---|---|---|---|---|---|---|---|---|---|---|
| | | | | 165 | | | | | 170 | | | | | 175 | |

| Asp | Val | Thr | Met | Phe | Phe | Gln | Lys | Ile | Ser | Leu | Gly | Asp | Cys | Lys | Met |
|---|---|---|---|---|---|---|---|---|---|---|---|---|---|---|---|
| | | | | 180 | | | | | 185 | | | | | 190 | |

| Trp | Leu | Glu | Glu | Phe | Leu | Met | Tyr | Trp | Gln | Met | Leu | Asp | Pro | Thr |
|---|---|---|---|---|---|---|---|---|---|---|---|---|---|---|
| | | | 195 | | | | | 200 | | | | | 205 | |

| Lys | Pro | Pro | Ser | Leu | Ala | Pro | Gly | Thr | Thr | Gln | Pro | Arg | Ser | Cys | Asp |
|---|---|---|---|---|---|---|---|---|---|---|---|---|---|---|---|
| | 210 | | | | | 215 | | | | | 220 | | | | |

| Lys | Thr | His | Thr | Cys | Pro | Pro | Cys | Pro | Ala | Pro | Glu | Ala | Glu | Gly | Ala |
|---|---|---|---|---|---|---|---|---|---|---|---|---|---|---|---|
| 225 | | | | | 230 | | | | | 235 | | | | | 240 |

| Pro | Ser | Val | Phe | Leu | Phe | Pro | Pro | Lys | Pro | Lys | Asp | Thr | Leu | Met | Ile |
|---|---|---|---|---|---|---|---|---|---|---|---|---|---|---|---|
| | | | | 245 | | | | | 250 | | | | | 255 | |

| Ser | Arg | Thr | Pro | Glu | Val | Thr | Cys | Val | Val | Val | Asp | Val | Ser | His | Glu |
|---|---|---|---|---|---|---|---|---|---|---|---|---|---|---|---|
| | | | 260 | | | | | 265 | | | | | 270 | | |

| Asp | Pro | Glu | Val | Lys | Phe | Asn | Trp | Tyr | Val | Asp | Gly | Val | Glu | Val | His |
|---|---|---|---|---|---|---|---|---|---|---|---|---|---|---|---|
| | | 275 | | | | | 280 | | | | | 285 | | | |

| Asn | Ala | Lys | Thr | Lys | Pro | Arg | Glu | Glu | Gln | Tyr | Asn | Ser | Thr | Tyr | Arg |
|---|---|---|---|---|---|---|---|---|---|---|---|---|---|---|---|
| | 290 | | | | | 295 | | | | | 300 | | | | |

| Val | Val | Ser | Val | Leu | Thr | Val | Leu | His | Gln | Asp | Trp | Leu | Asn | Gly | Lys |
|---|---|---|---|---|---|---|---|---|---|---|---|---|---|---|---|
| 305 | | | | | 310 | | | | | 315 | | | | | 320 |

| Glu | Tyr | Lys | Cys | Lys | Val | Ser | Asn | Lys | Ala | Leu | Pro | Ala | Pro | Ile | Glu |
|---|---|---|---|---|---|---|---|---|---|---|---|---|---|---|---|
| | | | | 325 | | | | | 330 | | | | | 335 | |

| Lys | Thr | Ile | Ser | Lys | Ala | Lys | Gly | Gln | Pro | Arg | Glu | Pro | Gln | Val | Tyr |
|---|---|---|---|---|---|---|---|---|---|---|---|---|---|---|---|
| | | | 340 | | | | | 345 | | | | | 350 | | |

| Thr | Leu | Pro | Pro | Ser | Arg | Asp | Glu | Leu | Thr | Lys | Asn | Gln | Val | Ser | Leu |
|---|---|---|---|---|---|---|---|---|---|---|---|---|---|---|---|
| | | 355 | | | | | 360 | | | | | 365 | | | |

| Thr | Cys | Leu | Val | Lys | Gly | Phe | Tyr | Pro | Ser | Asp | Ile | Ala | Val | Glu | Trp |
|---|---|---|---|---|---|---|---|---|---|---|---|---|---|---|---|
| | 370 | | | | | 375 | | | | | 380 | | | | |

-continued

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 6
<211> LENGTH: 453
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(223)
<223> OTHER INFORMATION: ULBP-2 sequences
<220> FEATURE:
<221> NAME/KEY: PEPTIDE
<222> LOCATION: (224)..(453)
<223> OTHER INFORMATION: Human Ig Fc sequences

<400> SEQUENCE: 6

Met Ala Ala Ala Ala Thr Lys Ile Leu Leu Cys Leu Pro Leu Leu
1               5                   10                  15

Leu Leu Leu Ser Gly Trp Ser Arg Ala Gly Arg Ala Asp Pro His Ser
            20                  25                  30

Leu Cys Tyr Asp Ile Thr Val Ile Pro Lys Phe Arg Pro Gly Pro Arg
        35                  40                  45

Trp Cys Ala Val Gln Gly Gln Val Asp Glu Lys Thr Phe Leu His Tyr
    50                  55                  60

Asp Cys Gly Asn Lys Thr Val Thr Pro Val Ser Pro Leu Gly Lys Lys
65                  70                  75                  80

Leu Asn Val Thr Thr Ala Trp Lys Ala Gln Asn Pro Val Leu Arg Glu
                85                  90                  95

Val Val Asp Ile Leu Thr Glu Gln Leu Arg Asp Ile Gln Leu Glu Asn
            100                 105                 110

Tyr Thr Pro Lys Glu Pro Leu Thr Leu Gln Ala Arg Met Ser Cys Glu
        115                 120                 125

Gln Lys Ala Glu Gly His Ser Ser Gly Ser Trp Gln Phe Ser Phe Asp
    130                 135                 140

Gly Gln Ile Phe Leu Leu Phe Asp Ser Glu Lys Arg Met Trp Thr Thr
145                 150                 155                 160

Val His Pro Gly Ala Arg Lys Met Lys Glu Lys Trp Glu Asn Asp Lys
                165                 170                 175

Val Val Ala Met Ser Phe His Tyr Phe Ser Met Gly Asp Cys Ile Gly
            180                 185                 190

Trp Leu Glu Asp Phe Leu Met Gly Met Asp Ser Thr Leu Glu Pro Ser
        195                 200                 205

Ala Gly Ala Pro Leu Ala Met Ser Ser Gly Thr Thr Gln Leu Arg Arg
    210                 215                 220

Ser Cys Asp Lys Thr His Thr Cys Pro Pro Cys Pro Ala Pro Glu Ala
225                 230                 235                 240

Glu Gly Ala Pro Ser Val Phe Leu Phe Pro Pro Lys Pro Lys Asp Thr
```

```
                    245                 250                 255
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
        450

<210> SEQ ID NO 7
<211> LENGTH: 270
<212> TYPE: PRT
<213> ORGANISM: Artificial Sequence
<220> FEATURE:
<223> OTHER INFORMATION: Peptides
<220> FEATURE:
<221> NAME/KEY: PEPTIDE
<222> LOCATION: (225)..(257)
<223> OTHER INFORMATION: leucine zipper motif
<220> FEATURE:
<221> NAME/KEY: PEPTIDE
<222> LOCATION: (1)..(19)
<223> OTHER INFORMATION: human Ig kappa signal peptide
<220> FEATURE:
<221> NAME/KEY: PEPTIDE
<222> LOCATION: (265)..(270)
<223> OTHER INFORMATION: polyhistidine
<220> FEATURE:
<221> NAME/KEY: PEPTIDE
<222> LOCATION: (258)..(264)
<223> OTHER INFORMATION: spacer
<220> FEATURE:
<221> NAME/KEY: PEPTIDE
<222> LOCATION: (20)..(218)
<223> OTHER INFORMATION: ULBP-1 sequences
<220> FEATURE:
<221> NAME/KEY: PEPTIDE
<222> LOCATION: (219)..(224)
<223> OTHER INFORMATION: spacer

<400> SEQUENCE: 7

Met Glu Thr Asp Thr Leu Leu Leu Trp Val Leu Leu Leu Trp Val Pro
1               5                   10                  15

Gly Ser Thr Gly Trp Ser Arg Ala Gly Trp Val Asp Thr His Cys Leu
```

-continued

```
                  20                  25                  30

Cys Tyr Asp Phe Ile Ile Thr Pro Lys Ser Arg Pro Glu Pro Gln Trp
                35                  40                  45

Cys Glu Val Gln Gly Leu Val Asp Glu Arg Pro Phe Leu His Tyr Asp
 50                  55                  60

Cys Val Asn His Lys Ala Lys Ala Phe Ala Ser Leu Gly Lys Lys Val
65                  70                  75                  80

Asn Val Thr Lys Thr Trp Glu Gln Thr Glu Thr Leu Arg Asp Val
                85                  90                  95

Val Asp Phe Leu Lys Gly Gln Leu Leu Asp Ile Gln Val Glu Asn Leu
                100                 105                 110

Ile Pro Ile Glu Pro Leu Thr Leu Gln Ala Arg Met Ser Cys Glu His
                115                 120                 125

Glu Ala His Gly His Gly Arg Gly Ser Trp Gln Phe Leu Phe Asn Gly
    130                 135                 140

Gln Lys Phe Leu Leu Phe Asp Ser Asn Asn Arg Lys Trp Thr Ala Leu
145                 150                 155                 160

His Pro Gly Ala Lys Lys Met Thr Glu Lys Trp Glu Lys Asn Arg Asp
                165                 170                 175

Val Thr Met Phe Phe Gln Lys Ile Ser Leu Gly Asp Cys Lys Met Trp
                180                 185                 190

Leu Glu Glu Phe Leu Met Tyr Trp Glu Gln Met Leu Asp Pro Thr Lys
                195                 200                 205

Pro Pro Ser Leu Ala Pro Gly Thr Thr Gln Pro Arg Ser Gly Ser Ser
    210                 215                 220

Arg Met Lys Gln Ile Glu Asp Lys Ile Glu Ile Leu Ser Lys Ile
225                 230                 235                 240

Tyr His Ile Glu Asn Glu Ile Ala Arg Ile Lys Lys Leu Ile Gly Glu
                245                 250                 255

Arg Gly Thr Ser Ser Arg Gly Ser His His His His His
                260                 265                 270
```

<210> SEQ ID NO 8
<211> LENGTH: 274
<212> TYPE: PRT
<213> ORGANISM: Artificial Sequence
<220> FEATURE:
<223> OTHER INFORMATION: Peptides
<220> FEATURE:
<221> NAME/KEY: PEPTIDE
<222> LOCATION: (1)..(223)
<223> OTHER INFORMATION: ULBP-2 sequences
<220> FEATURE:
<221> NAME/KEY: PEPTIDE
<222> LOCATION: (224)..(229)
<223> OTHER INFORMATION: spacer
<220> FEATURE:
<221> NAME/KEY: PEPTIDE
<222> LOCATION: (230)..(261)
<223> OTHER INFORMATION: leucine zipper motif
<220> FEATURE:
<221> NAME/KEY: PEPTIDE
<222> LOCATION: (262)..(268)
<223> OTHER INFORMATION: spacer
<220> FEATURE:
<221> NAME/KEY: PEPTIDE
<222> LOCATION: (269)..(274)
<223> OTHER INFORMATION: polyhistidine

<400> SEQUENCE: 8

```
Met Ala Ala Ala Ala Ala Thr Lys Ile Leu Leu Cys Leu Pro Leu Leu
1               5                   10                  15
```

```
Leu Leu Leu Ser Gly Trp Ser Arg Ala Gly Arg Ala Asp Pro His Ser
            20                  25                  30
Leu Cys Tyr Asp Ile Thr Val Ile Pro Lys Phe Arg Pro Gly Pro Arg
            35                  40                  45
Trp Cys Ala Val Gln Gly Gln Val Asp Glu Lys Thr Phe Leu His Tyr
 50                  55                  60
Asp Cys Gly Asn Lys Thr Val Thr Pro Val Ser Pro Leu Gly Lys Lys
 65                  70                  75                  80
Leu Asn Val Thr Thr Ala Trp Lys Ala Gln Asn Pro Val Leu Arg Glu
                 85                  90                  95
Val Val Asp Ile Leu Thr Glu Gln Leu Arg Asp Ile Gln Leu Glu Asn
            100                 105                 110
Tyr Thr Pro Lys Glu Pro Leu Thr Leu Gln Ala Arg Met Ser Cys Glu
            115                 120                 125
Gln Lys Ala Glu Gly His Ser Ser Gly Ser Trp Gln Phe Ser Phe Asp
            130                 135                 140
Gly Gln Ile Phe Leu Leu Phe Asp Ser Glu Lys Arg Met Trp Thr Thr
145                 150                 155                 160
Val His Pro Gly Ala Arg Lys Met Lys Glu Lys Trp Glu Asn Asp Lys
                165                 170                 175
Val Val Ala Met Ser Phe His Tyr Phe Ser Met Gly Asp Cys Ile Gly
                180                 185                 190
Trp Leu Glu Asp Phe Leu Met Gly Met Asp Ser Thr Leu Glu Pro Ser
            195                 200                 205
Ala Gly Ala Pro Leu Ala Met Ser Ser Gly Thr Thr Gln Leu Arg Gly
            210                 215                 220
Ser Gly Ser Ser Arg Met Lys Gln Ile Glu Asp Lys Ile Glu Glu Ile
225                 230                 235                 240
Leu Ser Lys Ile Tyr His Ile Glu Asn Glu Ile Ala Arg Ile Lys Lys
                245                 250                 255
Leu Ile Gly Glu Arg Gly Thr Ser Ser Arg Gly Ser His His His
            260                 265                 270
His His

<210> SEQ ID NO 9
<211> LENGTH: 950
<212> TYPE: DNA
<213> ORGANISM: Homo sapiens

<400> SEQUENCE: 9
agccccgcga tccttccgcg cctcgcgatt cttccgtacc tgctattcga ctggtccggg      60
acggggcggg ccgacgctca ctctctctgg tataacttca ccatcattca tttgcccaga    120
catgggcaac agtggtgtga ggtccagagc caggtggatc agaagaattt tctctcctat    180
gactgtggca gtgacaaggt cttatctatg ggtcacctag aagagcagct gtatgccaca    240
gatgcctggg aaaacaact  ggaaatgctg agagaggtgg ggcagaggct cagactggaa    300
ctggctgaca ctgagctgga ggatttcaca cccagtggac ccctcacgct gcaggtcagg    360
atgtcttgtg agtgtgaagc cgatggatac atccgtggat cttggcagtt cagcttcgat    420
ggacggaagt tcctcctctt tgactcaaac aacagaaagt ggacagtggt tcacgctgga    480
gccaggcgga tgaaagagaa gtgggagaag gatagcggac tgaccacctt cttcaagatg    540
gtctcaatga gagactgcaa gagctggctt agggacttcc tgatgcacag gaagaagagg    600
```

```
ctggaaccca cagcaccacc caccatggcc ccaggcttag ctcaacccaa agccatagcc      660
accaccctca gtccctggag cttcctcatc atcctctgct tcatcctccc tggcatctga      720
gaagagtcat ttagagtgac aggtggaagg tgatatcaag aagcctctgt tagcctggtc      780
tggttcctgc tctcccttca gggaggccgc ctgtctactc accactgtgc ctttctggaa      840
agcaggagtt caagcttag caagcccaga ggcccccagc agatgatgag gacattgtcg       900
gctcaacgtc tcaggccact cattaccttc gctcatgatc ccagcagcca                950
```

<210> SEQ ID NO 10
<211> LENGTH: 239
<212> TYPE: PRT
<213> ORGANISM: Homo sapiens

<400> SEQUENCE: 10

```
Ser Pro Ala Ile Leu Pro Arg Leu Ala Ile Leu Pro Tyr Leu Leu Phe
1               5                   10                  15

Asp Trp Ser Gly Thr Gly Arg Ala Asp Ala His Ser Leu Trp Tyr Asn
            20                  25                  30

Phe Thr Ile Ile His Leu Pro Arg His Gly Gln Gln Trp Cys Glu Val
        35                  40                  45

Gln Ser Gln Val Asp Gln Lys Asn Phe Leu Ser Tyr Asp Cys Gly Ser
    50                  55                  60

Asp Lys Val Leu Ser Met Gly His Leu Glu Glu Gln Leu Tyr Ala Thr
65                  70                  75                  80

Asp Ala Trp Gly Lys Gln Leu Glu Met Leu Arg Glu Val Gly Gln Arg
                85                  90                  95

Leu Arg Leu Glu Leu Ala Asp Thr Glu Leu Glu Asp Phe Thr Pro Ser
            100                 105                 110

Gly Pro Leu Thr Leu Gln Val Arg Met Ser Cys Glu Cys Glu Ala Asp
        115                 120                 125

Gly Tyr Ile Arg Gly Ser Trp Gln Phe Ser Phe Asp Gly Arg Lys Phe
    130                 135                 140

Leu Leu Phe Asp Ser Asn Asn Arg Lys Trp Thr Val Val His Ala Gly
145                 150                 155                 160

Ala Arg Arg Met Lys Glu Lys Trp Glu Lys Asp Ser Gly Leu Thr Thr
                165                 170                 175

Phe Phe Lys Met Val Ser Met Arg Asp Cys Lys Ser Trp Leu Arg Asp
            180                 185                 190

Phe Leu Met His Arg Lys Arg Leu Glu Pro Thr Ala Pro Pro Thr
        195                 200                 205

Met Ala Pro Gly Leu Ala Gln Pro Lys Ala Ile Ala Thr Thr Leu Ser
    210                 215                 220

Pro Trp Ser Phe Leu Ile Ile Leu Cys Phe Ile Leu Pro Gly Ile
225                 230                 235
```

<210> SEQ ID NO 11
<211> LENGTH: 8
<212> TYPE: PRT
<213> ORGANISM: Artificial Sequence
<220> FEATURE:
<223> OTHER INFORMATION: FLAG peptide

<400> SEQUENCE: 11

```
Asp Tyr Lys Asp Asp Asp Lys
1               5
```

```
<210> SEQ ID NO 12
<211> LENGTH: 27
<212> TYPE: PRT
<213> ORGANISM: Artificial Sequence
<220> FEATURE:
<223> OTHER INFORMATION: Leucine zipper

<400> SEQUENCE: 12

Pro Asp Val Ala Ser Leu Arg Gln Gln Val Glu Ala Leu Gln Gly Gln
1               5                  10                  15

Val Gln His Leu Gln Ala Ala Phe Ser Gln Tyr
            20                  25

<210> SEQ ID NO 13
<211> LENGTH: 33
<212> TYPE: PRT
<213> ORGANISM: Artificial Sequence
<220> FEATURE:
<223> OTHER INFORMATION: Leucine zipper peptide

<400> SEQUENCE: 13

Arg Met Lys Gln Ile Glu Asp Lys Ile Glu Glu Ile Leu Ser Lys Ile
1               5                  10                  15

Tyr His Ile Glu Asn Glu Ile Ala Arg Ile Lys Lys Leu Ile Gly Glu
            20                  25                  30

Arg

<210> SEQ ID NO 14
<211> LENGTH: 6
<212> TYPE: PRT
<213> ORGANISM: Artificial Sequence
<220> FEATURE:
<223> OTHER INFORMATION: Peptide spacer

<400> SEQUENCE: 14

Pro Arg Ser Gly Ser Ser
1               5
```

ULBP DNA AND POLYPEPTIDES

CROSS-REFERENCE TO RELATED APPLICATIONS

This application is a continuation in part of PCT/US98/27048, filed Dec. 17, 1998, currently pending, which claims priority from U.S. Ser. No. provisional application No. 60/069,857, filed Dec. 17, 1997 and U.S. Ser. No. provisional application No. 60/092,946, filed Jul. 15, 1998.

BACKGROUND OF THE INVENTION

1. Field of the Invention

The invention is directed to purified and isolated polypeptides, the nucleic acids encoding the polypeptides, and processes for production of recombinant forms of the polypeptides. This invention is also directed to antibodies that specifically recognize the polypeptides, compositions containing the polypeptides, and to the use of these materials in various assays. In particular, the polypeptides, the nucleic acids encoding the polypeptides, and the antibodies are useful for the detection of human B cell lymphomas, enhancing the production of interferon γ (IFN-γ), enhancing the growth of NK cells, treating viral infections and tumors, and enhancing the activity of cytotoxic T lymphocytes (CTLs).

2. Description of Related Art

1. Lymphomas

The malignant lymphomas represent multiple diseases with diverse morphologic and clinical expressions. Morphologic classification schemes have been shown to be useful in delineating natural history, prognosis, and response to therapy. However, in some instances, distinctive morphologic entities may be very closely related clinically or biologically or both, whereas other diseases that share morphologic similarities may be clinically and biologically quite distinct. Thus, immunological methods have become essential tools for the diagnosis and classification of certain human tumors, particularly for leukemias and lymphomas.

More particularly, some patients carrying malignancies have been found to produce antibodies against tumor-associated or other malignant cell-associated surface determinants as well as against a variety of differentiation and other non-tumor antigens. Several very sensitive immunological procedures have been developed for the detection of such antibodies.

A variety of other markers of hematopoietic malignancies allows clinically valuable categorizations, which are not possible by morphological or histochemical parameters. These markers can also be detected using immunological procedures. One of the main advantages of these procedures over other methods for the measurement of tumor-associated markers is their high level of sensitivity, with the ability often to detect a substance at nanogram or even picogram levels. In addition, immunological tests afford the ability to discriminate among substances with closely related structures and thereby to identify tumor-associated analogs found in normal, nonmalignant states.

Many tumor-associated markers have been detected in the sera or other body fluids of patients with malignancies. A few of these markers have been sufficiently restricted to tumor-bearing individuals to aid in detection or differential diagnosis (or both) of malignant disease. However, most markers have been found to lack sufficient specificity for such applications, with an appreciable frequency of elevated marker levels in patients with nonmalignant diseases (i.e., false positive results).

In addition, malignant lymphomas are usually an admixture of a neoplastic element and normal elements or both. A cell suspension prepared from a malignant lymphoma will consist of a mixture of benign and malignant cells, and the malignant cells may not necessarily be in the majority. To determine the phenotype of malignant cells, it is necessary to identify those markers associated with neoplastic cells.

It should be evident that there exists a need in the art for the identification of additional cell surface markers associated with malignant conditions. In particular, there is a continuing need for cell surface markers associated with malignant lymphomas. The identification of specific cell surface markers associated with malignant lymphomas will aid the detection of malignancies associated with these markers.

2. NK cells

One of the major types of circulating mononuclear cells is that of the natural killer, or NK, cell (M. Manoussaka et al., *Journal of Immunology* 158:112–119, 1997). NK cells are a cell type derived from bone marrow precursors (O. Haller et al., *Journal of Experimental Medicine* 145:1411–1420, 1977). NK cells appear to be closely related to T cells and the two cell types share many cell surface markers (M. Manoussaka et al., 1997). Although NK cells are cytotoxic cells as are some T cells, unlike T cells, NK cells do not express the T-cell receptor or CD3 components (P. Scott and G. Trinichieri, *Current Opinion in Immunology* 7:34–40, 1995; G. Trinichieri, *Adv. Immunology* 47:187–376, 1989). NK cells commonly express CD16 and CD56 antigens (K. Oshimi, *International Journal of Hematology* 63:279–290, 1996). Similar to cytotoxic T lymphocytes (CTL), NK cells are capable of exerting a cytotoxic effect by lysing a variety of cell types (G. Trinichieri, 1989). NK cells are capable of exerting cytotoxicity in a non-MHC restricted fashion (E. Ciccione et al., J. Exp. Med. 172:47, 1990; A. Moretta et al., J. Exp. Med. 172:1589, 1990; and E. Ciccione et al., J. Exp. Med. 175:709).

NK cells mediate some of their functions through the secretion of cytokines, such as interferon γ (IFNγ), granulocyte-macrophage colony-stimulating factors (GM-CSFs), tumor necrosis factor α (TNF-α), macrophage colony-stimulating factor (M-CSF), interleukin-3 (IL-3), and IL-8 (P. Scott and G. Trinichieri, 1995).

Cytokines including IL-2, IL-12, TNF-α and IL-1 can induce NK cells to produce cytokines (P. Scott and G. Trinichieri, 1995). IFNγ and IL-2 are strong inducers of NK cell cytotoxic activity (G. Trinichieri et al., *Journal of Experimental Medicine* 160:1147–1169, 1984; G. Trinichieri and D. Santoli, *Journal of Experimental Medicine* 147:1314–1333, 1977). NK cells can be stimulated and expanded in the presence of IL-2 (K. Oshimi, *International Journal of Hematology* 63:279–290, 1996). IL-12 has been shown to induce cytokine production from T and NK cells, and augment NK cell-mediated cytotoxicity (M. Kobayashi et al., *Journal of Experimental Medicine* 170:827–846, 1989).

NK cells can lyse a variety of cell types, including normal stem cells, infected cells, and transformed cells (D. See et al., *Scand. J. Immunol.* 46:217–224, 1997). Cells that lack MHC class I are susceptible to NK cell-mediated lysis (H. Reyburn et al.,*Immunol. Rev.* 155:119–125, 1997). The lysis of cells occurs through the action of cytoplasmic granules containing proteases, nucleases, and perforin (D. See et al., 1997). Antibodies directed against CD2 and CD11a inhibit the cytotoxic effect of NK cells (0. Ramos et al.,*J. Immunol.* 142:4100–4104, 1989; C. Scott et al., *J. Immunol.* 142:4105–4112, 1989). NK cells can also lyse cells by antibody-dependent cellular cytotoxicity (D. See et al., 1997).

NK cells have been shown to destroy both extracellular protozoa and the cells infected by protozoa (T. Scharton- Kersten and A. Sher, *Current Opinion in Immunology* 9:44–51, 1997). In most instances, cytotoxic activity appears to be dependent upon lymphokine activation (T. Scharton-Kersten and A. Sher, 1997).

NK cells have been implicated as mediators of host defenses against infection in humans with varicella zoster, herpes simplex, cytomegalovirus, Epstein-Barr virus, hepatitis B, and hepatitis C viruses (D. See et al., 1997). Many viruses induce NK cell cytotoxicity, including herpesvirus and cytomegalovirus (C. Biron, *Current Opinion in Immunology* 9:24–34, 1997). The induction of NK cell activity is a result of the induction of IFN-γ by viral infection, and NK cells are important in the early defense against many viral infections (C. Biron, 1997). The NK1+CD3-population of NK cells is the subset activated by viral infection (C. Biron, 1997). The response of NK cells to viral infection involves direct cytotoxicity and production of various cytokines such as IFN-γ and TNF-α (C. Biron, 1997).

A number of human lymphoproliferative disorders of NK cells are known. These include NK cell-lineage granular lymphocyte proliferative disorder (NK-GLPD), NK cell lymphoma, and acute leukemia of NK cell lineage (K. Oshimi, *International Journal of Hematology* 63:279–290, 1996). Most patients with aggressive type NK-GLPD die of the disease (K. Oshimi, 1996). NK cell lymphoma is resistant to combination chemotherapy (K. Oshimi, 1996).

NK cells activated with IL-2 have been shown to have activity against human leukemia cells (L. Silla et al., *Journal of Hematotherapy* 4:269–279, 1995). Furthermore, NK cells appear to have a role in the treatment of chronic myeloid leukemia (K. Oshimi, 1996).

NK cells are involved in both the resistance to and control of cancer spread (T. Whiteside and R. Herberman, *Current Opinion in Immunology* 7:704–710, 1995). Furthermore, the presence and activation of NK cells may be outcome determinative; low or non-existent NK activity is associated with a high frequency of viral disease and cancer (T. Whiteside and R. Herberman, 1995).

In view of the important role that NK and T cells play in vivo, in host defenses, tumor cell surveillance, and autoimmune diseases, there exists a need in the art for polypeptides suitable for the in vivo and in vitro enhancement of NK and T cell activity.

3. Interferon γ

The production of IFNγ is a function of T cells and NK cells, and IFN-γ activates antiviral immune reactions (E. De Maeyer and J. De Maeyer-Guignard, in *The Cytokine Handbook*, A. W. Thompson (ed.), Academic Press, 1994, pp. 265–288). IFN-γ preferentially inhibits Th2 proliferation, but not Th1 proliferation (T. F. Gajewski and F. W. Fitch, *J. Immunology* 140:4245–4252, 1988). IFN-γ also plays an important role in macrophage activation and promotes proliferation of activated B cells (De Maeyer and De Maeyer-Guignard). These, and other effects of IFN-γ, indicate that increased in vivo levels of IFNγ production serve as a general immune modulator.

IFN-γ has been used clinically in treating chronic granulomatous disease, atopic dermatitis, systemic achlerosis, lepratmatous leprosy, common warts, hepatitis B infection, myelogenous leukemia, and metastatic melanoma (J. Mordenti et al., in *Therapeutic Proteins*, A. H. C. Kung et al. (eds.), W. H. Freeman and Co., 1993, pp.187–199). In view of the important role that IFN-γ plays, in vivo, in immune modulation, there exists a need in the art for polypeptides suitable for the enhancement of in vivo and in vitro IFN-γ levels.

4. Cytotoxic T Lymphocytes

CTLs are an important in vivo defense against viral, and bacterial, and cancerous diseases, in that they lyse target cells bearing foreign antigens (G. Berke, in *Fundamental Immunology*, W. E. Paul (ed.) Raven Press Ltd., 1989, pp. 735–764. In view of the important role that CTLs plays, in vivo, in the immune response to infections and tumor surveillance, there exists a need in the art for polypeptides suitable for the enhancement of in vivo and in vitro CTL activity.

SUMMARY OF THE INVENTION

The invention aids in fulfilling these various needs in the art by providing isolated ULBP nucleic acids and polypeptides encoded by these nucleic acids. Specifically, one embodiment of this invention provides cell surface glycoproteins associated with human B cell lymphomas. In a broad sense, this invention pertains to novel polypeptides referred to herein as ULBP polypeptides, which are found on the surface of human B cell lymphomas. The present invention is specifically directed to mammalian forms of ULBP polypeptides in isolated and purified forms. Particular embodiments of the invention are directed to isolated ULBP nucleic acid molecules comprising the DNA sequence of SEQ ID NO:1, SEQ ID NO:3, or SEQ ID NO:9 and isolated ULBP nucleic acid molecules encoding the amino acid sequence of SEQ ID NO:2, SEQ ID NO:4, or SEQ ID NO:10, as well as nucleic acid molecules complementary to these sequences. Both single-stranded and double-stranded RNA and DNA nucleic acid molecules are encompassed by the invention, as well as nucleic acid molecules that hybridize to a denatured, double-stranded DNA comprising all or a portion of SEQ ID NO:1, SEQ ID NO:3, and/or SEQ ID NO:9. Also encompassed are isolated nucleic acid molecules that are derived by in vitro mutagenesis of nucleic acid molecules comprising sequences of SEQ ID NO:1, SEQ ID NO:3, or SEQ ID NO:9, that are degenerate from nucleic acid molecules comprising sequences of SEQ ID NO:1, SEQ ID NO:3, or SEQ ID NO:9, and that are allelic variants of DNA of the invention. The invention also encompasses recombinant vectors that direct the expression of these nucleic acid molecules and host cells stably or transiently transformed or transfected with these vectors.

In addition, the invention encompasses methods of using the nucleic acids noted above to identify nucleic acids encoding proteins having ULBP activity; to identify human chromosome number 6; to map genes on human chromosome number 6; to identify genes associated with certain diseases, syndromes, or other human conditions associated with human chromosome number 6, and to study cell signal transduction and the ULBP system.

The invention also encompasses the use of sense or antisense oligonucleotides from the nucleic acid of SEQ ID NO:1, SEQ ID NO:3, or SEQ ID NO:9 to inhibit the expression of the polynucleotide encoded by the ULBP gene.

The invention also encompasses isolated polypeptides and fragments thereof encoded by these nucleic acid molecules including soluble polypeptide portions of SEQ ID NO:1, SEQ ID NO:3, or SEQ ID NO:9. The invention further encompasses methods for the production of these polypeptides, including culturing a host cell under conditions promoting expression and recovering the polypeptide from the culture medium. Especially, the expression of these polypeptides in bacteria, yeast, plant, insect, and animal cells is encompassed by the invention.

In general, the polypeptides of the invention can be used to study cellular processes such as immune regulation, cell proliferation, cell death, cell migration, cell-to-cell interaction, and inflammatory responses. In addition, these polypeptides can be used to identify proteins associated with ULBP ligands and ULBP receptors.

In yet another aspect, the invention includes assays utilizing these polypeptides to screen for potential inhibitors of activity associated with polypeptide counter-structure molecules, and methods of using these polypeptides as therapeutic agents for the treatment of diseases mediated by ULBP polypeptide counter-structure molecules. Further, methods of using these polypeptides in the design of inhibitors thereof are also an aspect of the invention.

Another aspect of this invention is the use of the ULBP nucleic acid sequences, predicted amino acid sequences of the polypeptide or fragments thereof, or a combination of the predicted amino acid sequences of the polypeptide and fragments thereof for use in searching an electronic database to aid in the identification of sample nucleic acids and/or proteins.

Isolated polyclonal or monoclonal antibodies that bind to these polypeptides are also encompassed by the invention, in addition to the use of these antibodies to aid in purifying the ULBP polypeptide. The antibodies, in turn, are useful for detecting the presence of ULBP polypeptides in human cell samples, which can be correlated with the existence of a malignant condition in a patient.

More generally, this invention provides methods of detecting B cell lymphomas using the polypeptides, DNA, and antibodies of the invention. The methods are based, for example, on immunological and DNA hybridization and amplification techniques.

Furthermore, this invention provides in vitro and in vivo methods of increasing IFN-γ production, increasing NK cell proliferation and activation, and increasing CTL activity. In connection with NK cell activity, the ULBP polypeptides disclosed herein find utility as antiviral and antitumor therapeutics

DETAILED DESCRIPTION OF THE INVENTION

ULBP DNAs encode cell-surface glycoproteins. cDNAs encoding human ULBP polypeptides have been isolated and cloned from human cells. The discovery of these DNAs encoding human ULBP polypeptides enables construction of expression vectors comprising nucleic acids encoding these polypeptides; host cells transfected or transformed with the expression vectors; biologically active human ULBP polypeptides as isolated and purified proteins and polypeptides; and antibodies immunoreactive with the polypeptides.

In one particular embodiment of the invention, a ULBP gene designated ULBP-1 was expression cloned from a Namalwa (human B cell lymphoma) cDNA library. This was accomplished by binding to a UL16-Fc fusion protein. UL16 is a type I membrane glycoprotein encoded by human cytomegalovirus (Kaye et al., J. Virol. 66:6609, 1992). UL16-Fc fuses the extracellular domain of UL16 to the IgG1 Fc (mutein form) as previously described for OX40-Fc (Baum et al., EMBO J. 13:3992–4001, 1994). Expression cloning of ULBP-1 was carried out using standard techniques previously described for CD27L and OX40L (Cell 73:447, 1993, EMBO J. 13:3992–4001, 1994). The entire disclosure of each of these references is relied upon and incorporated by reference herein.

The nucleotide sequence of the ULBP-1 gene (coding region only) in Staden format is as follows:

[SEQ ID NO:1]
ATGGCAGCGGCCGCCAGCCCCGCCTTCCTTCTGTGCCTCCCGCTTCTGCA

CCTGCTGTCTGGCTGGTCCCGGGCAGGATGGGTCGACACACACTGTCTTT

GCTATGACTTCATCATCACTCCTAAGTCCAGACCTGAACCACAGTGGTGT

GAAGTTCAAGGCCTGGTGGATGAAAGGCCTTTTCTTCACTATGACTGTGT

TAACCACAAGGCCAAAGCCTTTGCTTCTCTGGGGAAGAAAGTCAATGTCA

CAAAAACCTGGGAAGAACAAACTGAAACACTAAGAGACGTGGTGGATTTC

CTTAAAGGGCAACTGCTTGACATTCAAGTGGAGAATTTAATACCCATTGA

GCCCCTCACCCTGCAGGCCAGGATGTCTTGTGAGCATGAAGCCCATGGAC

ACGGCAGAGGATCTTGGCAGTTCCTCTTCAATGGACAGAAGTTCCTCCTC

TTTGACTCAAACAACAGAAAGTGGACAGCACTTCATCCTGGAGCCAAGAA

GATGACAGAGAAGTGGGAGAAGAACAGGGATGTGACCATGTTCTTCCAGA

AGATTTCACTGGGGGATTGTAAGATGTGGCTTGAAGAATTTTTGATGTAC

TGGGAACAAATGCTGGATCCAACAAAACCACCCTCTCTGGCCCCAGGCAC

AACCCAACCCAAGGCCATGGCCACCACCCTCAGTCCCTGGAGCCTTCTCA

TCATCTTCCTCTGCTTCATTCTAGCTGGCAGATGA.

The polypeptide encoded by the nucleotide of SEQ ID NO: 1 has an amino acid sequence as follows:

```
MAAAASPAFL LCLPLLHLLS GWSRAGWVDT HCLCYDFIIT PKSRPEPQWC   [SEQ ID NO:2]
EVQGLVDERP FLHYDCVNHK AKAFASLGKK VNvTKTWEEQ TETLRDVVDF
LKGQLLDIQV ENLIPIEPLT LQARMSCEHE AHGHGRGSWQ FLFNGQKFLL
FDSNNRKWTA LHPGAKKMTE KWEKNRDVTM FFQKISLGDC KMWLEEFLMY
WEQMLDPTKP PSLAPGTTQP KAAATTLSPW SLLIIFLCFI LAGR.
```

The isolated and purified ULBP-1 polypeptide of the invention has a molecular weight of approximately 31 kD as determined by SDS-polyacrylamide gel electrophoresis (SDS-PAGE). The signal peptide of ULBP-1 polypeptide (amino acids 1–21) can be cleaved to provide a mature protein beginning at aa 22.

In another distinct embodiment of the invention, a ULBP gene designated ULBP-2 was recognized as an EST homologous to the ULBP-1 gene (GenBank accession number R25716). The sequence in the EST database was not correct. Moreover, this EST was not recognized as encoding a protein related to any other protein. The EST clone was obtained and sequenced completely, revealing that it encoded a full length protein sequence.

The nucleotide sequence of the ULBP-2 gene (coding sequence only) is as follows:

[SEQ ID NO:3]
ATGGCAGCAGCCGCCGCTACCAAGATCCTTCTGTGCCTCCCGCTTCTGCT

CCTGCTGTCCGGCTGGTCCCGGGCTGGGCGAGCCGACCCTCACTCTCTTT

GCTATGACATCACCGTCATCCCTAAGTTCAGACCTGGACCACGGTGGTGT

GCGGTTCAAGGCCAGGTGGATGAAAAGACTTTTCTTCACTATGACTGTGG

-continued

```
CAACAAGACAGTCACACCTGTCAGTCCCCTGGGGAAGAAACTAAATGTCA

CAACGGCCTGGAAAGCACAGAACCCAGTACTGAGAGAGGTGGTGGACATA

CTTACAGAGCAACTGCGTGACATTCAGCTGGAGAATTACACACCCAAGGA

ACCCCTCACCCTGCAGGCAAGGATGTCTTGTGAGCAGAAAGCTGAAGGAC

ACAGCAGTGGATCTTGGCAGTTCAGTTTCGATGGGCAGATCTTCCTCCTC

TTTGACTCAGAGAAGAGAATGTGGACAACGGTTCATCCTGGAGCCAGAAA

GATGAAAGAAAAGTGGGAGAATGACAAGGTTGTGGCCATGTCCTTCCATT

ACTTCTCAATGGGAGACTGTATAGGATGGCTTGAGGACTTCTTGATGGGC

ATGGACAGCACCCTGGAGCCAAGTGCAGGAGCACCACTCGCCATGTCCTC

AGGCACAACCCAACTCAGGGCCACAGCCACCACCCTCATCCTTTGCTGCC

TCCTCATCATCCTCCCCTGCTTCATCCTCCCTGGCATCTGA.
```

The polypeptide encoded by SEQ ID NO:3 has the following amino acid sequence:

```
MAAAAATKIL  LCLPLLLLLS  GWSRAGRADP  HSLCYDITVI  PKFRPGPRWC    [SEQ ID NO:4]

AVQGQVDEKT  FLHYDCGNKT  VTPVSPLGKK  LNVTTAWKAQ  NPVLREVVDI

LTEQLRDIQL  ENYTPKEPLT  LQARMSCEQK  AEGHSSGSWQ  FSFDGQIFLL

FDSEKRMWTT  VHPGARKMKE  KWENDKVVAM  SFHYFSMGDC  IGWLEDFLMG

MDSTLEPSAG  APLAMSSGTT  QLRATATTLI  LCCLLIILPC  FILPGI.
```

The isolated and purified ULBP-2 polypeptide according to the invention has a molecular weight of approximately 31 kD as determined by SDS-polyacrylamide gel electrophoresis (SDS-PAGE). In the case of this polypeptide, cleavage of the signal peptide occurs between amino acids 21 and 22.

The ULBP-1 and ULBP-2 polypeptides are 60% identical at the amino acid level. The similarities and differences in their sequences are evident from the following sequence alignment of amino acids 1–243 of SEQ ID NO:2 with amino acids 1–245 of SEQ ID NO:4:

In another distinct embodiment of the invention, a ULBP gene designated ULBP-3 was recognized as an EST homologous to the ULBP-1 gene (GenBank accession number AI091180). The EST clone was obtained and sequenced completely, revealing that it encoded a protein sequence, which lacked the first five amino acids of the leader sequence. The nucleotide sequence of the ULBP-3 gene is as follows:

```
ULBP-1    1 MAAAASPAFLLCLPLLHLLSGWSRAGWVDTHCLCYDFIITPKSRPEPQWC
            |||||.. :|||||||  ||||||||||:.|.|:|||:.:.||  ||:|.||
ULBP-2    1 MAAAAATKILLCLPLLLLLSGWSRAGRADPHSLCYDITVIPKFRPGPRWC

51 EVQGLVDERPFLHYDCVNHKAKAFASLGKKVNVTKTWEEQTETLKDVVDF
            .||||||:.||||||.|....:....||||:|||..|..|...||:|||:
         51 AVQGQVDEKTFLHYDCGNKTVTPVSPLGKKLNVTTAWKAQNPVLREVVDI

101 LKGQLLDIQVENLIPIEPLTLQARMSCEHEAHGHGRGSWQFLFNGQKFLL
            |.:||  |||:||..|  |||||||||||||:.|.||:.|||||  |:|| |||
        101 LTEQLRDIQLENYTPKEPLTLQARMSCEQKAEGHSSGSWQFSFDGQIFLL

151 FDSNNRKWTALHPGAKKMTEKWEKNRDVTMFFQKISLGDCKMWLEEFLMY
            |||:.|.||.:|||||:||.||||.:: |.| |; :|:||| |||:|||
        151 FDSEKRMWTTVHPGARKMKEKWENDKVVAMSFHYFSMGDCIGWLEDFLMG

201 WEQMLDPTKPPSLA..PGTTQPKAMATTLSPWSLLIIFLCFILAG 243
            : |:|. .:.|| .|||| :| ||||    :|||:  ||||:|
        201 MDSTLEPSAGAPLAMSSGTTQLRATATTLILCCLLIILPCFILPG 245
```

```
AGCCCCGCGA TCCTTCCGCG CCTCGCGATT CTTCCGTACC TGCTATTCGA    [SEQ ID NO:9]

CTGGTCCGGG ACGGGCGGG CCGACGCTCA CTCTCTCTGG TATAACTTCA

CCATCATTCA TTTGCCCAGA CATGGGCAAC AGTGGTGTGA GGTCCAGAGC

CAGGTGGATC AGAAGAATTT TCTCTCCTAT GACTGTGGCA GTGACAAGGT

CTTATCTATG GGTCACCTAG AAGAGCAGCT GTATGCCACA GATGCCTGGG

GAAAACAACT GGAAATGCTG AGAGAGGTGG GGCAGAGGCT CAGACTGGAA

CTGGCTGACA CTGAGCTGGA GGATTTCACA CCCAGTGGAC CCCTCACGCT

GCAGGTCAGG ATGTCTTGTG AGTGTGAAGC CGATGGATAC ATCCGTGGAT

CTTGGCAGTT CAGCTTCGAT GGACGGAAGT TCCTCCTCTT TGACTCAAAC

AACAGAAAGT GGACAGTGGT TCACGCTGGA GCCAGGCGGA TGAAAGAGAA

GTGGGAGAAG GATAGCGGAC TGACCACCTT CTTCAAGATG GTCTCAATGA

GAGACTGCAA GAGCTGGCTT AGGGACTTCC TGATGCACAG GAAGAAGAGG

CTGGAACCCA CAGCACCACC CACCATGGCC CCAGGCTTAG CTCAACCCAA

AGCCATAGCC ACCACCCTCA GTCCCTGGAG CTTCCTCATC ATCCTCTGCT

TCATCCTCCC TGGCATCTGA GAAGAGTCAT TTAGAGTGAC AGGTGGAAGG

TGATATCAAG AAGCCTCTGT TAGCCTGGTC TGGTTCCTGC TCTCCCTTCA

GGGAGGCCGC CTGTCTACTC ACCACTGTGC CTTTCTGGAA AGCAGGAGTT

CAAGCCTTAG CAAGCCCAGA GGCCCCCAGC AGATGATGAG GACATTGTCG

GCTCAACGTC TCAGGCCACT CATTACCTTC GCTCATGATC CCAGCAGCCA
```

The equivalent amino acid sequence of ULBP-3 is:

```
SPAILPRLAI LPYLLFDWSG TGRADAHSLW YNFTIIHLPR HGQQWCEVQS    [SEQ ID NO:10]
QVDQKNFLSY DCGSDKVLSM GHLEEQLYAT DAWGKQLEML REVGQRLRLE
LADTELEDFT PSGPLTLQVR MSCECEADGY IRGSWQFSFD GRKFLLFDSN
NRKWTVVHAG ARRMKEKWEK DSGLTTFFKM VSMRDCKSWL RDFLMHRKKR
LEPTAPPTMA PGLAQPKAIA TTLSPWSFLI ILCFILPGI
```

The ULBP-3 is a member of the ULBP family. ULBP-1 and ULBP-3 are 54% identical, and ULBP-2 and ULBP-3 are 54% identical, which is evident from the following sequence alignments of the amino acid sequences of ULBP-1 (SEQ ID NO:2), ULBP-2 (SEQ ID NO:4), and ULBP-3 (SEQ ID NO:10):

```
         1                                                    50
ULBP1    MAAAASPAFL LCLPLL.HLL SGWSRAGWVD THCLCYDFII TPKSRPEPQW
ULBP2    MAAAAATKIL LCLPLL.LLL SGWSRAGRAD PHSLCYDITV IPKFRPGPRW
ULBP3    ~~~~SPAIL PRLAILPYLL FDWSGTGRAD AHSLWYNFTI IHLPRHGQQW 51                                                  100
ULBP1    CEVQGLVDER PFLHYDCVNH KAKAFASLGK KVNVTKTWEE QTETLRDVVD
ULBP2    CAVQGQVDEK TFLHYDCGNK TVTPVSPLGK KLNVTTAWKA QNPVLREVVD
ULBP3    CEVQSQVDQK NFLSYDCGSD KVLSMGHLEE QLYATDAWGK QLEMLREVGQ 101                                                 150
ULBP1    FLKGQLLDIQ VENLIPIEPL TLQARMSCEH EAHGHGRGSW QFLFNGQKFL
ULBP2    ILTEQLRDIQ LENYTPKEPL TLQARMSCEQ KAEGHSSGSW QFSFDGQIFL
ULBP3    RLRLELADTE LEDFTPSGPL TLQVRMSCEC EADGYIRGSW QFSFDGRKFL 151                                                 200
ULBP1    LFDSNNRKWT ALHPGAKKMT EKWEKNRDVT MFFQKISLGD CKMWLEEFLM
ULBP2    LFDSEKRMWT TVHPGARKMK EKWENDKVVA MSFHYFSMGD CIGWLEDFLM
ULBP3    LFDSNNRKWT VVHAGARRMK EKWEKDSGLT TFFKMVSMRD CKSWLRDFLM
```

```
         201                                              248
ULBP1  YWEQMLDPT. .KPPSLAPGT TQPKAMATTL SPWSLLIIFL CFILAGR*
ULBP2  GMDSTLEPSA GAPLAMSSGT TQLRATATTL ILCCLLIILP CFILPGI*
ULBP3  HRKKRLEPTA ..PPTMAPGL AQPKAIATTL SPWSFLIIL. CFILPGI*

ULBP1    1  MAAAASPAFLLCLPLL.HLLSGWSRAGWVDTHCLCYDFIITPKSRPEPQW  49
            |||.|  |.:|  ||  .||  .|:  |.|  |  |:|  |    .|    ||
ULBP3    1  .....SPAILPRLAILPYLLFDWSGTGRADAHSLWYNFTIIHLPRHGQQW  45

50  CEVQGLVDERPFLHYDCVNHKAKAFASLGKKVNVTKTWEEQTETLRDVVD  99
            ||||.  ||::  ||  |||  ..|    ..  |    .:    |   .|    |   |   |:|   :
        46  CEVQSQVDQKNFLSYDCGSDKVLSMGHLEEQLYATDAWGKQLENLREVGQ  95

100  FLKGQLLDIQVENLIPIEPLTLQARMSCEHEAHGHGRGSWQFLFNGQKFL  149
            |: :|  |  ::|::  |    |||||  ||||||  ||.|   ||||||   |:|.|||
        96  RLRLELADTELEDFTPSGPLTLQVRMSCECEADGYIRGSWQFSFDGRKFL  145

150  LFDSNNRKWTALHPGAKKNTEKWEKNRDVTMFFQKISLGDCKMWLEEFLM  199
            ||||||||||   :|.||::|   |||||:  .:|   ||.  :|:   |||   ||   :|||
       146  LFDSNNRKWTVVHAGARRMKEKWEKDSGLTTFFKNVSMRDCKSWLRDFLM  195

200  YWEQMLDPTKPPSLAPGTTQPKAMATTLSPWSLLIIFLCFILAGR*  245
            :  .  |:||   ||.:|||   .|||||:||||||||||:|||   ||||||.|   |
       196  HRKKRLEPTAPPTMAPGLAQPKAIATTLSPWSFLII.LCFILPGI*  240

ULBP2    1  MAAAAATKILLCLPLL.LLLSGWSRAGRADPHSLCYDITVIPKFRPGPRW  49
              .    ||  |.:|   ||  .||  .||||.|||   |:.|:|    |  |  .|
ULBP3    1  .....SPAILPRLAILPYLLFDWSGTGRADAHSLWYNFTIIHLPRHGQQW  45

50  CAVQGQVDEKTFLHYDCGNKTVTPVSPLGKKLNVTTAWKAQNPVLREVVD  99
            |   ||.|||:|   ||   ||||.    |    .:.    |    .|    |   ||    |   :||||    :
        46  CEVQSQVDQKNFLSYDCGSDKVLSMGHLEEQLYATDAWGKQLEMLREVGQ  95

100  ILTEQLRDIQLENYTPKEPLTLQARMSCEQKAEGHSSGSWQFSFDGQIFL  149
            |   :|   |  :||::||   |||||  ||||||   |:|   |||||||||.  ||
        96  RLRLELADTELEDFTPSGPLTLQVRMSCECEADGYIRGSWQFSFDGRKFL  145

150  LFDSEKRMWTTVHPGARKMKEKWENDKVVAMSFHYFSNGDCIGWLEDFLM  199
            ||||..|   ||   ||.|||:||||||.|   :.    |      ||   ||  .||  ||||
       146  LFDSNNRKWTVVHAGARRMKEKWEKDSGLTTFFKMVSMRDCKSWLRDFLM  195

200  GMDSTLEPSAGAPLAMSSGTTQLRATATTLILCCLLIILPCFILPGI*  247
            |||.   ||  .|..|   .|   :|   ||||      :||||   ||||||||
       196  HRKKRLEPT..APPTMAPGLAQPKAIATTLSPWSFLIIL.CFILPGI*  240
```

A "|" indicates identity of amino acids, a "." indicates weak conservation of amino acids, and a ":" indicates high conservation of amino acids, as determined by alignment of the sequences using the GCG GAP program with the pep scoring matrix, gap creation penalty=30, gap extension penalty=1.

ULBP-1, ULBP-2, and ULBP-3 polypeptides are distantly related to a number of MHC class 1 proteins, particularly non-classical class I molecules or class 1 molecules of non-human species. ULBP-1, ULBP-2, and ULBP-3 polypeptides contain regions homologous to the α1 and α2 domains of MHC class I proteins. However, they have a different structure from other class I molecules in that they lack the alpha-3 domain, which is needed for binding beta-2-microglobulin. The α1 domain is approximately from amino acids 30–117 for ULBP-1 and ULBP-2, and approximately from amino acids 26–113 for ULBP-3. The α2 domain is approximately from amino acids 118–200 for ULBP-1 and ULBP-2, and approximately from amino acids 114–196 for ULBP-3 In addition, the ULBP-1 and the ULBP-2 genes map to chromosome 6q20-26, which is distinct from any other MHC class 1 and related genes.

It will be understood that ULBP DNA and proteins and polypeptides encoded by the DNA are not limited to ULBP-1, ULBP-2, and ULBP-3. More particularly, the term "ULBP DNA" refers to a genus of polynucleotides having the same sequence as SEQ ID NO:1, SEQ ID NO:3, and SEQ ID NO:9, as well as those polynucleotides having a high degree of similarity (at least 90% homology) with such DNA sequences.

Similarly, the term "ULBP polypeptide" refers to a genus of polypeptides and proteins having the same amino acid sequences as SEQ ID NO:2, SEQ ID NO:4, or SEQ ID NO:10 as well as polypeptides and proteins having a high degree of similarity (at least 90% identity) with such amino acid sequences and which proteins are biologically active. ULBP polypeptides also include biologically active gene products of polynucleotides of SEQ ID NO:1, SEQ ID NO:3, and SEQ ID NO:9. When used herein, the term "ULBP" is intended to encompass ULBP DNA, as well as ULBP polypeptides.

The discovery of the nucleic acids of the invention enables the construction of expression vectors comprising nucleic acid sequences encoding polypeptides; host cells transfected or transformed with the expression vectors; isolated and purified biologically active polypeptides and fragments thereof; the use of the nucleic acids or oligonucleotides thereof as probes to identify nucleic acid encoding proteins having ULBP activity, the use of the nucleic acids or oligonucleotides thereof to identify human chromosome number 6, the use of the nucleic acids or oligonucleotides thereof to map genes on human chromosome number 6, the use of the nucleic acid or oligonucleotides thereof to identify genes associated with certain diseases, syndromes or other human conditions associated with human chromosome number 6 (including Retinitis pigmentosa-25 (6q14-q21); Diabetes mellitus, insulin-dependent,15 (6q21); Progressive pseudorheumatoid arthropathy of childhood (6q22); Muscular dystrophy, congenital merosin-deficient (6q22-q23); and Cardiomyopathy, dilated, 1F (6q23)), and the use of single-stranded sense or antisense oligonucleotides from the nucleic acids to inhibit expression of polynucleotide encoded by ULBP genes.

NUCLEIC ACID MOLECULES

In a particular embodiment, the invention relates to certain isolated nucleic molecules that are free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual*, 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NO:1, SEQ ID NO:3, or SEQ ID NO:9, or a suitable fragment thereof, as a probe.

The DNA molecules of the invention include full length genes as well as polynucleotides and fragments thereof. The full length gene may include the N-terminal signal peptide. Other embodiments include DNA encoding a soluble form, e.g., encoding the extracellular domain of the protein, either with or without the signal peptide and/or the GPI linkage.

The nucleic acids of the invention are preferentially derived from human sources, but the invention includes those derived from non-human species, as well.

Preferred DNAs

Particularly preferred nucleic acids of the invention are described in SEQ ID NO:1, SEQ ID NO:3, and SEQ ID NO:9, as set forth above. The polypeptide encoded by SEQ ID NO:1 has the amino acid sequence shown in SEQ ID NO:2. The polypeptide encoded by SEQ ID NO:3 has the amino acid sequence shown in SEQ ID NO:4. The polypeptide encoded by SEQ ID NO:9 has the amino acid sequence shown in SEQ ID NO:10. These sequences identify the ULBP-1, ULBP-2, and ULBP-3 polynucleotides as a member of the ULBP family.

Additional DNAs and Polypeptides

Due to the known degeneracy of the genetic code, wherein more than one codon can encode the same amino acid, a DNA can vary from that shown in SEQ ID NO:1, SEQ ID NO:3, and SEQ ID NO:9, and still encode a polypeptide having the amino acid sequence of SEQ ID NO:2, SEQ ID NO:4, and SEQ ID NO:10. Such variant DNAs can result from silent mutations (e.g., occurring during PCR amplification), or can be the product of deliberate mutagenesis of a native sequence.

The invention thus provides isolated DNAs encoding polypeptides of the invention, selected from: (a) DNA comprising the nucleotide sequence of SEQ ID NO:1, SEQ ID NO:3, or SEQ ID NO:9; (b) DNA encoding the polypeptides of SEQ ID NO:2, SEQ ID NO:4, or SEQ ID NO:10.; (c) DNA capable of hybridization to a DNA of (a) or (b) under conditions of moderate stringency and which encodes active polypeptides of the invention; (d) DNA capable of hybridization to a DNA of (a) or (b) under conditions of high stringency and which encodes active polypeptides of the invention, and (e) DNA which is degenerate as a result of the genetic code to a DNA defined in (a), (b), (c), or (d) and which encode active polypeptides of the invention. Of course, polypeptides encoded by such DNA sequences are encompassed by the invention.

The invention thus provides equivalent isolated DNAs encoding active ULBP polypeptides selected from: (a) DNA derived from the coding region of a native mammalian ULBP gene; (b) DNA selected from the group consisting of nucleotide residues 1–735 of SEQ ID NO:1, nucleotide residues 1–741 of SEQ ID NO:3, and nucleotide residues 1–717 of SEQ ID NO:9 (c) DNA capable of hybridization to a DNA of (a) or (b) under conditions of moderate stringency and which encodes biologically active ULBP polypeptides; and (d) DNA that is degenerate as a result of the genetic code to a DNA defined in (a), (b) or (c), and which encodes biologically active ULBP polypeptides. ULBP polypeptides encoded by such DNA equivalents are encompassed by the invention. ULBP polypeptides encoded by DNA derived from other mammalian species, wherein the DNA will hybridize to the complement of the DNA of SEQ ID NO:1, SEQ ID NO:3, or SEQ ID NO:9, are also encompassed.

As used herein, conditions of moderate stringency can be readily determined by those having ordinary skill in the art based on, for example, the length of the DNA. The basic conditions are set forth by Sambrook et al. *Molecular Cloning:A Laboratory Manual*, 2 ed. Vol. 1, pp. 1.101–104, Cold Spring Harbor Laboratory Press, (1989), and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

Also included as an embodiment of the invention is DNA encoding polypeptide fragments and polypeptides comprising inactivated N-glycosylation site(s), inactivated protease processing site(s), or conservative amino acid substitution(s), as described below.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence encoding a ULBP polypeptide, or desired fragment thereof may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., *Science* 239:487 (1988); *Recombinant DNA Methodology*, Wu et al., eds., Academic Press, Inc., San Diego (1989), pp. 189–196; and *PCR Protocols: A Guide to Methods and Applications*, Innis et al., eds., Academic Press, Inc. (1990).

POLYPEPTIDES AND FRAGMENTS THEREOF

The invention encompasses polypeptides and fragments thereof in various forms, including those that are naturally occurring or produced through various techniques such as procedures involving recombinant DNA technology. For example, DNAs encoding ULBP polypeptides can be derived from SEQ ID NO:1, SEQ ID NO:3, or SEQ ID NO:9 by in vitro mutagenesis, which includes site-directed mutagenesis, random mutagenesis, and in vitro nucleic acid synthesis. Such forms include, but are not limited to, derivatives, variants, and oligomers, as well as fusion proteins or fragments thereof.

Polypeptides and Fragments Thereof

The polypeptides of the invention include full length proteins encoded by the nucleic acid sequences set forth above. Particularly preferred polypeptides comprise the amino acid sequence of SEQ ID NO:2, SEQ ID NO:4, and SEQ ID NO:10, with particularly preferred fragments comprising amino acids from about amino acid 22 to about amino acid 219 of SEQ ID NO:2 and from about amino acid 22 to about amino acid 223 of SEQ ID NO:4.

The polypeptides of SEQ ID NO:2, SEQ ID NO:4, and SEQ ID NO:10 includes an N-terminal hydrophobic region that functions as a signal peptide. Computer analysis predicts that the signal peptide corresponds to residues 1 to 21 of SEQ ID NO:2 and SEQ ID NO:4, and residues 1–17 of SEQ ID NO:10. Cleavage of the signal peptide thus would yield a mature protein comprising amino acids 22 through 244 of SEQ ID NO:2, amino acids 22 through 246 of SEQ ID NO:4, and amino acids 17 through 239 of SEQ ID NO:10. The skilled artisan will recognize that the above-described boundaries of such regions of the polypeptide are approximate, and that the boundaries of the regions (which may be predicted by using computer programs available for that purpose) may differ from those described above.

The polypeptides of SEQ ID NO:2, SEQ ID NO:4, and SEQ ID NO:10 includes a C-terminal hydrophobic region that functions as a GPI linkage. The predicted GPI linkage approximately corresponds to the last 20 residues of SEQ ID NO:2, SEQ ID NO:4, and SEQ ID NO:10. Removal of the GPI linkage thus would yield a protein comprising amino acids 1 through about 224 of SEQ ID NO:2, 1 through about 226 of SEQ ID NO:4, and 1 through about 219 of SEQ ID NO:10. Removal of both the signal peptide and the GPI linkage thus would yield a protein comprising amino acids from about 22 through about 224 of SEQ ID NO:2, from about 22 through about 226 of SEQ ID NO:4, and from about 17 through about 219 of SEQ ID NO:10. The skilled artisan will recognize that the above-described boundaries of such regions of the polypeptide are approximate, and may differ from those described above.

The polypeptides of the invention may be membrane bound or they may be secreted and thus soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

In one embodiment, the soluble polypeptides and fragments thereof comprise all or part of the extracellular domain, but lack the GPI linkage that would cause retention of the polypeptide on a cell membrane. A soluble polypeptide may include a portion of the GPI linkage, as long as the polypeptide is secreted from the cell in which it is produced.

Soluble polypeptides thus include, but are not limited to, polypeptides comprising amino acids having an N-terminus at amino acid 20–30 and a C-terminus at amino acids 200–227 of SEQ ID NO:2, an N-terminus at amino acid 20–30 and a C-terminus at amino acids 200–227 of SEQ ID NO:4, and an N-terminus at amino acid 16–26 and a C-terminus at amino acids 196–223 of SEQ ID NO:10.

In general, the use of soluble forms is advantageous for certain applications. Purification of the polypeptides from recombinant host cells is facilitated, since the soluble polypeptides are secreted from the cells. Further, soluble polypeptides are generally more suitable for intravenous administration.

The invention also provides polypeptides and fragments of the extracellular domain that retain a desired biological activity. Particular embodiments are directed to polypeptide fragments that retain the ability to bind ULBP counter-structures, such as UL16. Such a fragment may be a soluble polypeptide, as described above. In another embodiment, the polypeptides and fragments advantageously include regions that are conserved in the ULBP family as described above.

Also provided herein are polypeptide fragments comprising at least 20, or at least 30, contiguous amino acids of the sequence of SEQ ID NO:2, SEQ ID NO:4, or SEQ ID NO:10. Polypeptide fragments also may be employed as immunogens, in generating antibodies.

Variants

Naturally occurring variants as well as derived variants of the polypeptides and fragments are provided herein.

An "ULBP variant" as referred to herein means a polypeptide substantially homologous to native ULBP polypeptide, but which has an amino acid sequence different from that of native ULBP polypeptide (human, murine or other mammalian species) because of one or more deletions, insertions, or substitutions. The variant has an amino acid sequence that preferably is at least 80% identical to a native ULBP polypeptide amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Variants also include embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined as above. Alternatively, the percent identity of two protein sequences can be determined by comparing sequence information using the GAP computer program, based on the algorithm of Needleman and Wunsch (J. Mol. Bio. 48:443, 1970) and available from the University of Wisconsin Genetics Computer Group (UWGCG). The preferred default parameters for the GAP program include: (1) a scoring matrix, blosum62, as described by Henikoff and Henikoff (Proc. Natl. Acad. Sci. USA 89:10915, 1992); (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. Alternate splicing of mRNA may, for example, yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1–5 terminal amino acids). Proteins in which differences in amino acid sequence are attributable to genetic polymorphism (allelic variation among individuals producing the protein) are also contemplated herein.

As stated above, the invention provides isolated and purified, or homogeneous, ULBP polypeptides, both recombinant and non-recombinant. Variants and derivatives of native ULBP proteins that retain the desired biological activity can be obtained by mutations of nucleotide sequences coding for native ULBP polypeptides. Alterations of the native amino acid sequence can be accomplished by any of a number of conventional methods. Mutations can be introduced at particular loci by synthesizing oligonucleotides containing a mutant sequence flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene, wherein predetermined codons can be altered by substitution, deletion, or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, all of which are incorporated by reference.

ULBP polypeptides can be modified to create ULBP derivatives by forming covalent or aggregative conjugates with other chemical moieties, such as glycosyl groups, polyethylene glycol (PEG) groups, lipids, phosphate, acetyl groups and the like. Covalent derivatives of ULBP polypeptides can be prepared by linking the chemical moieties to functional groups on ULBP amino acid side chains or at the N-terminus or C-terminus of a ULBP polypeptide or the extracellular domain thereof. Other derivatives of ULBP polypeptides within the scope of this invention include covalent or aggregative conjugates of ULBP polypeptides or their fragments with other proteins or polypeptides, such as by synthesis in recombinant culture as N-terminal or C-terminal fusions. For example, the conjugate can comprise a signal or leader polypeptide sequence (e.g. the γ-factor leader of Saccharomyces) at the N-terminus of a ULBP polypeptide. The signal or leader peptide co-translationally or post-translationally directs transfer of the conjugate from its site of synthesis to a site inside or outside of the cell membrane or cell wall.

Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (SEQ ID NO:11), which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259.

Among the variant polypeptides provided herein are variants of native polypeptides that retain the native biological activity or the substantial equivalent thereof. One example is a variant that binds with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Further, a given preparation may include multiple differentially glycosylated species of the protein. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, similar DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in proteins include those described in U.S. Pat. No. 5,071,972 and EP 276,846, hereby incorporated by reference.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Oligomers

Encompassed by the invention are oligomers or fusion proteins that contain ULBP polypeptides. Such oligomers may be in the form of covalently-linked or non-covalently-linked multimers, including dimers, trimers, or higher oligomers. As noted above, preferred polypeptides are soluble and thus these oligomers may comprise soluble polypeptides. In one aspect of the invention, the oligomers maintain the binding ability of the polypeptide components and provide therefor, bivalent, trivalent, etc., binding sites.

One embodiment of the invention is directed to oligomers comprising multiple polypeptides joined via covalent or non-covalent interactions between peptide moieties fused to the polypeptides. Such peptides may be peptide linkers (spacers), or peptides that have the property of promoting oligomerization. Leucine zippers and certain polypeptides derived from antibodies are among the peptides that can promote oligomerization of the polypeptides attached thereto, as described in more detail below.

Immunoglobulin-based Oligomers

As one alternative, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Proteins", in *Current Protocols in Immnmunology*, Suppl. 4, pages 10.19.1–10.19.11, 1992).

One embodiment of the present invention is directed to a dimer comprising two fusion proteins created by fusing a polypeptide of the invention to an Fc polypeptide derived from an antibody. A gene fusion encoding the polypeptide/Fc fusion protein is inserted into an appropriate expression vector. Polypeptide/Fc fusion proteins are expressed in host cells transformed with the recombinant expression vector, and allowed to assemble much like antibody molecules, whereupon interchain disulfide bonds form between the Fc moieties to yield divalent molecules.

The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred polypeptides comprise an Fc polypeptide derived from a human IgG1 antibody.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J*. 13:3992–4001, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

The above-described fusion proteins comprising Fc moieties (and oligomers formed therefrom) offer the advantage of facile purification by affinity chromatography over Protein A or Protein G columns.

In other embodiments, the polypeptides of the invention may be substituted for the variable portion of an antibody heavy or light chain. If fusion proteins are made with both heavy and light chains of an antibody, it is possible to form an oligomer with as many as four ULBP extracellular regions.

Both ULBP-1 and ULBP-2 polypeptides can be expressed as Fc fusion proteins using an Fc mutein to provide fused polypeptides having the following sequences:

```
MAAAASPAFL LCLPLLHLLS GWSRAGWVDT HCLCYDFIIT PKSRPEPQWC    [SEQ ID NO: 5]
EVQGLVDERP FLHYDCVNHK AKAFASLGKK VNVTKTWEEQ TETLRDVVDF
LKGQLLDIQV ENLIPIEPLT LQARMSCEHE AHGHGRGSWQ FLFNGQKFLL
FDSNNRKWTA LHPGAKKMTE KWEKNRDVTM FFQKISLGDC KMWLEEFLMY
WEQMLDPTKP PSLAPGTTQP RSCDKTHTCP PCPAPEAEGA PSVFLFPPKP
KDTLMISRTP EVTCVVVDVS HEDPEVKFNW YVDGVEVHNA KTKPREEQYN
STYRVVSVLT VLHQDWLNGK EYKCKVSNKA LPAPIEKTIS KAKGQPREPQ
VYTLPPSRDE LTKNQVSLTC LVKGFYPSDI AVEWESNGQP ENNYKTTPPV
LDSDGSFFLY SKLTVDKSRW QQGNVFSCSV MHEALHNHYT QKSLSLSPGK;

MAAAAATKIL LCLPLLLLLS GWSRAGRADP HSLCYDITVI PKFRPGPRWC    [SEQ ID NO:6]
AVQGQVDEKT FLHYDCGNKT VTPVSPLGKK LNVTTAWKAQ NPVLREVVDI
LTEQLRDIQL ENYTPKEPLT LQARMSCEQK AEGHSSGSWQ FSFDGQIFLL
FDSEKRMWTT VHPGARKMKE KWENDKVVAM SFHYFSMGDC IGWLEDFLMG
MDSTLEPSAG APLAMSSGTT QLRRSCDKTH TCPPCPAPEA EGAPSVFLFP
PKPKDTLMIS RTPEVTCVVV DVSHEDPEVK FNWYVDGVEV HNAKTKPREE
QYNSTYRVVS VLTVLHQDWL NGKEYKCKVS NKALPAPIEK TISKAKGQPR
EPQVYTLPPS RDELTKNQVS LTCLVKGFYP SDIAVEWESN GQPENNYKTT
PPVLDSDGSF FLYSKLTVDK SRWQQGNVFS CSVMHEALHN HYTQKSLSLS
PGK.
```

ULBP-1, ULBP-2 and ULBP-3 are membrane-bound glycoproteins that are held on the cell surface by a GPI linkage. See Yan et al., *J. Mol. Biol*. 275:25–33 (1998) and Medof et al. FASEB J. 10:574–86 (1996). The approximately 20 carboxy-terminal amino acids of the ULBP polypeptides specify the GPI linkage. The deletion of these amino acids in the ULBP-1, ULBP-2 and ULBP-3 proteins (or Fc fusion proteins) results in proteins lacking the GPI linkage.

The invention encompasses ULBP polypeptides and fragments lacking the GPI linkage. A preferred ULBP polypeptide fragment comprises at least 6 contiguous amino acids of an amino acid sequence. In other embodiments, a preferred ULBP polypeptide fragment comprises at least 10, at least 20, or at least 100 contiguous amino acids of an amino acid sequence. These polypeptides can be produced in soluble form.

Both ULBP-1 and ULBP-2 bind UL16-Fc. In addition, ULBP-1, ULBP-2 and ULBP-3 bind to a number of human cell types, including mitogen-stimulated human T cells and natural killer (NK) cells. It has also been discovered that the ULBP-Fc proteins bind to K299 cells, an anaplastic lymphoma. ULBP1-Fc binds better than ULBP2-Fc.

Fusion proteins of the present invention can be anti-viral or anti-tumor therapeutics that include any of the ULBP polypeptides or soluble fragments, thereof, that are capable of activating NK cell killing, linked to an antibody or an antibody derivative. For anti-tumor therapeutics, preferred antibodies for linking to ULBP polypeptides or suitable soluble ULBP fragments are those recognizing tumor antigens on tumors that are targeted for killing by NK cells. Fusion proteins that incorporate a ULBP polypeptide or ULBP fragment capable of activating NK cells for killing and an antibody that recognizes tumor antigens, will bind to tumors and attract and activate NK cells to enhance tumor killing. Anti-viral therapeutics of the present invention include ULBP polypeptides or ULBP fragments capable of activating NK cells fused to an antibody specific for the virus of interest. Such an anti-viral therapeutic will enhance NK cell killing of the virus. Antibody derivatives can be fused to suitable ULBP polypeptides or ULBP polypeptide fragments to form useful therapeutics as just described. Suitable antibody derivatives include single chain Fvs, Fabs, and diabodies having biological activities that enhance the targeting power of the therapeutic. The fusion proteins are preferably covalently linked as described above.

Peptide-linker Based Oligomers

Alternatively, the oligomer is a fusion protein comprising multiple polypeptides, with or without peptide linkers (spacer peptides). Among the suitable peptide linkers are those described in U.S. Pat. Nos. 4,751,180 and 4,935,233, which are hereby incorporated by reference. A DNA sequence encoding a desired peptide linker may be inserted between, and in the same reading frame as, the DNA sequences of the invention, using any suitable conventional technique. For example, a chemically synthesized oligonucleotide encoding the linker may be ligated between the sequences. In particular embodiments, a fusion protein comprises from two to four soluble ULBP polypeptides, separated by peptide linkers.

Leucine-zippers

Another method for preparing the oligomers of the invention involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimenize.

The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit zipper domains, as does the gene product of the murine proto-oncogene, c-myc (Landschulz et al., *Science* 240:1759, 1988). The products of the nuclear oncogenes fos and jun comprise zipper domains that preferentially form heterodimer (O'Shea et al., *Science* 245:646, 1989, Turner and Tjian, *Science* 243:1689, 1989). The zipper domain is necessary for biological activity (DNA binding) in these proteins.

The fusogenic proteins of several different viruses, including paramyxovirus, coronavirus, measles virus and many retroviruses, also possess zipper domains (Buckland and Wild, *Nature* 338:547,1989; Britton, *Nature* 353:394, 1991; Delwart and Mosialos, *AIDS Research and Human Retroviruses* 6:703, 1990). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88:3523, 1991). Zipper domains have also been recently reported to play a role in oligomerization of heat-shock transcription factors (Rabindran et al., *Science* 259:230, 1993).

Zipper domains fold as short, parallel coiled coils (O'Shea et al., *Science* 254:539; 1991). The general architecture of the parallel coiled coil has been well characterized, with a "knobs-into-holes" packing as proposed by Crick in 1953 (*Acta Crystallogr.* 6:689). The dimer formed by a zipper domain is stabilized by the heptad repeat, designated (abcdefg)$_n$ according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix.

The residues at position d (often leucine) contribute large hydrophobic stabilization energies, and are important for oligomer formation (Krystek: et al., *Int. J. Peptide Res.* 38:229, 1991). Lovejoy et al. (*Science* 259:1288, 1993) recently reported the synthesis of a triple-stranded α-helical bundle in which the helices run up-up-down. Their studies confirmed that hydrophobic stabilization energy provides the main driving force for the formation of coiled coils from helical monomers. These studies also indicate that electrostatic interactions contribute to the stoichiometry and geometry of coiled coils. Further discussion of the structure of leucine zippers is found in Harbury et al. (*Science* 262:1401, Nov. 26, 1993).

Examples of leucine zipper domains suitable for producing soluble oligomeric proteins are described in PCT application WO 94/10308, and the leucine zipper derived from lung surfactant protein D (SPD) described in Hoppe et al. (*FEBS Letters* 344:191, 1994), hereby incorporated by reference. The use of a modified leucine zipper that allows for stable trimerization of a heterologous protein fused thereto is described in Fanslow et al. (*Semin. Immunol.* 6:267–278, 1994). Recombinant fusion proteins comprising a soluble polypeptide fused to a leucine zipper peptide are expressed in suitable host cells, and the soluble oligomer that forms is recovered from the culture supernatant.

Certain leucine zipper moieties preferentially form trimers. One example is a leucine zipper derived from lung surfactant protein D (SPD), as described in Hoppe et al. (*FEBS Letters* 344:191, 1994) and in U.S. Pat. No. 5,716,805, hereby incorporated by reference in their entirety. This lung SPD-derived leucine zipper peptide comprises the amino acid sequence Pro Asp Val Ala Ser Leu Arg Gln Gln Val Glu Ala Leu Gln Gly Gln Val Gln His Leu Gln Ala Ala Phe Ser Gln Tyr (SEQ ID NO: 12).

Another example of a leucine zipper that promotes trimerization is a peptide comprising the amino acid sequence Arg Met Lys Gln Be Glu Asp Lys Ile Glu Glu Ile Leu Set Lys Ile Tyr His Ile Glu Asn Glu Ile Ala Arg Ile Lys Lys Leu Ile Gly Glu Arg (SEQ ID NO:13), as described in U.S. Pat. No.

5,716,805. In one alternative embodiment, an N-terminal Asp residue is added; in another, the peptide lacks the N-terminal Arg residue.

Fragments of the foregoing zipper peptides that retain the property of promoting oligomerization may be employed as well. Examples of such fragments include, but are not limited to, peptides lacking one or two of the N-terminal or C-terminal residues presented in the foregoing amino acid sequences. Leucine zippers may be derived from naturally occurring leucine zipper peptides, e.g., via conservative substitution(s) in the native amino acid sequence, wherein the peptide's ability to promote oligomerization is retained.

Other peptides derived from naturally occurring trimeric proteins may be employed in preparing trimeric ULBP. Alternatively, synthetic peptides that promote oligomerization may be employed. In particular embodiments, leucine residues in a leucine zipper moiety are replaced by isoleucine residues. Such peptides comprising isoleucine may be referred to as isoleucine zippers, but are encompassed by the term "leucine zippers" as employed herein.

Both ULBP-1, ULBP-2, and ULBP-3 polypeptides can be expressed as leucine zipper fusion proteins using a leucine zipper motif. The following are sequences for representative ULBP1-LZ and ULBP2-LZ, it being understood that additional leucine zippers are also suitable for preparing leucine zipper fusion proteins. A corresponding ULBP3-LZ, has the same leucine zipper sequence fused to ULBP-3.

Amino acids 1–223 are from ULBP-2 polypeptide (SEQ ID NO:4), including its native signal peptide, and the spacers, leucine zipper, and poly His are the same as indicated above.

PRODUCTION OF POLYPEPTIDES AND FRAGMENTS THEREOF

Expression, isolation and purification of the polypeptides and fragments of the invention may be accomplished by any suitable technique, including but not limited to the following:

Expression Systems

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional

ULBP1-LZ FUSION POLYPEPTIDE

```
  1 METDTLLLWV LLLWVPGSTG WSRAGWVDTH CLCYDFIITP KSRPEPQWCE  [SEQ ID NO:7]

51 VQGLVDERPF LHYDCVNHKA KAFASLGKKV NVTKTWEEQT ETLRDVVDFL

101 KGQLLDIQVE NLIPIEPLTL QARMSCEHEA HGHGRGSWQF LFNGQKFLLF

151 DSNNRKWTAL HPGAKKMTEK WEKNRDVTMF FQKISLGDCK MWLEEFLMYW

201 EQMLDPTKPP SLAPGTTQPR SGSSRMKQIE DKIEEILSKI YHIENEIARI

251 KKLIGERGTS SRGSHHHHHH
```

Amino acids 1–19 are the signal peptide from the human Ig kappa that replace the ULBP-1 signal peptide. This improves expression somewhat, but the native ULBP-1 signal peptide could also be used, as well as other heterologous signal peptides. Amino acids 20–218 are from ULBP-1 (SEQ ID NO:2), followed by a short spacer, PRSGSS (SEQ ID: NO:14), the leucine zipper (strictly isoleucine zipper) from amino acids 225–257, a spacer, and six histidines to act as a tag for purification.

or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of

ULBP2-LZ FUSION POLYPEPTIDE

```
  1 MAAAAATKIL LCLPLLLLLS GWSRAGRADP HSLCYDITVI PKFRPGPRWC  [SEQ ID NO:8]

51 AVQGQVDEKT FLHYDCGNKT VTPVSPLGKK LNVTTAWKAQ NPVLREVVDI

101 LTEQLRDIQL ENYTPKEPLT LQARMSCEQK AEGHSSGSWQ FSFDGQIFLL

151 FDSEKRMWTT VHPGARKMKE KWENDKVVAM SFHYFSMGDC IGWLEDFLMG

201 MDSTLEPSAG APLAMSSGTT QLRGSGSSRM KQIEDKIEEI LSKIYHIENE

251 IARIKKLIGE RGTSSRGSHH HHHH
``` replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium*, and various other species within the genera Pseudomonas, Streptomyces, and Staphylococcus. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

ULBP DNA may be cloned in-frame into the multiple cloning site of an ordinary bacterial expression vector. Ideally the vector would contain an inducible promoter upstream of the cloning site, such that addition of an inducer leads to high-level production of the recombinant protein at a time of the investigator's choosing. For some proteins, expression levels may be boosted by incorporation of codons encoding a fusion partner (such as hexahistidine) between the promoter and the gene of interest. The resulting "expression plasmid" may be propagated in a variety of strains of *E. coli*.

For expression of the recombinant protein, the bacterial cells are propagated in growth medium until reaching a pre-determined optical density. Expression of the recombinant protein is then induced, e.g. by addition of IPTG (isopropyl-b-D-thiogalactopyranoside), which activates expression of proteins from plasmids containing a lac operator/promoter. After induction (typically for 1–4 hours), the cells are harvested by pelleting in a centrifuge, e.g. at 5,000×G for 20 minutes at 4° C.

For recovery of the expressed protein, the pelleted cells may be resuspended in ten volumes of 50 mM Tris-HCl (pH 8)/1 M NaCl and then passed two or three times through a French press. Most highly expressed recombinant proteins form insoluble aggregates known as inclusion bodies. Inclusion bodies can be purified away from the soluble proteins by pelleting in a centrifuge at 5,000×G for 20 minutes, 4° C. The inclusion body pellet is washed with 50 mM Tris-HCl (pH 8)/1% Triton X-100 and then dissolved in 50 mM Tris-HCl (pH 8)/8 M urea/0.1 M DTTf. Any material that cannot be dissolved is removed by centrifugation (10,000×G for 20 minutes, 20° C.). The protein of interest will, in most cases, be the most abundant protein in the resulting clarified supernatant. This protein may be "refolded" into the active conformation by dialysis against 50 mM Tris-HCl (pH 8)/5 mM $CaCl_2$/5 mM $Zn(OAc)_2$/1 mM GSSG/0.1 mM GSH. After refolding, purification can be carried out by a variety of chromatographic methods, such as ion exchange or gel filtration. In some protocols, initial purification may be carried out before refolding. As an example, hexahistidine-tagged fusion proteins may be partially purified on immobilized Nickel.

While the preceding purification and refolding procedure assumes that the protein is best recovered from inclusion bodies, those skilled in the art of protein purification will appreciate that many recombinant proteins are best purified out of the soluble fraction of cell lysates. In these cases, refolding is often not required, and purification by standard chromatographic methods can be carried out directly.

Yeast Systems

Alternatively, the polypeptides may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.*

255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or Insect Systems

Mammalian or insect host cell culture systems also may be employed to express recombinant polypeptides. Baccu-lovirus systems for production of heterologous proteins in insect cells are reviewed by Luckow and-Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture*, 1990, pp. 15–69). Additional protocols using commercially available reagents, such as Lipofectamine lipid reagent (Gibco/BRL) or Lipofectamine-Plus lipid reagent, can be used to transfect cells (Feigner et al., *Proc. Natl. Acad. Sci. USA* 84:7413–7417, 1987). In addition, electroporation can be used to transfect mammalian cells using conventional procedures, such as those in Sambrook et al. (*Molecular Cloning: A Laboratory Manual*, 2 ed. Vol. 1–3, Cold Spring Harbor Laboratory Press, 1989).

Selection of stable transformants can be performed using methods known in the art, such as, for example, resistance to cytotoxic drugs. Kaufman et al., *Meth. in Enzymology* 185:487–511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216–4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529–534 and PCT Application WO 97/25420) and the tripartite leader (TPL) and VA gene RNAs from Adenovirus 2 (Gingeras et al., *J. Biol. Chem.* 257:13475–13491, 1982). The internal ribosome entry site (IRES) sequences of viral origin allows dicistronic mRNAs to be translated efficiently (Oh and Samnow, *Current Opinion in Genetics and Development* 3:295–300, 1993; Ramesh et al., *Nucleic Acids Research* 24:2697–2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150–161, 1997, and p2A5I described by Morris et al., *Animal Cell Technology*, 1997, pp. 529–534.

A useful high expression vector, pCAVNOT, has been described by Mosley et al., *Cell* 59:335–348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1 kD), hydrophilic, FLAG® marker peptide to the N-terminus of a recombinant protein expressed by pFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Regarding signal peptides that may be employed, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-I receptor signal peptide described in U.S. Pat. No. 4,968,607; and the type II interleukin-1 receptor signal peptide described in EP 460,846.

Purification

The invention also includes methods of isolating and purifying the polypeptides and fragments thereof. An isolated and purified ULBP polypeptide according to the invention can be produced by recombinant expression systems as described above or purified from naturally occurring cells. ULBP polypeptide can be substantially purified, as indicated by a single protein band upon analysis by SDS-polyacrylamide gel electrophoresis (SDS-PAGE). One process for producing ULBP comprises culturing a host cell transformed with an expression vector comprising a DNA sequence that encodes ULBP polypeptide under conditions sufficient to promote expression of ULBP. ULBP polypeptide is then recovered from culture medium or cell extracts, depending upon the expression system employed.

Isolation and Purification

The expression "isolated and purified" as used herein means that ULBP is essentially free of association with other DNA, proteins, or polypeptides, for example, as a purification product of recombinant host cell culture or as a purified product from a non-recombinant source. The term "substantially purified" as used herein refers to a mixture that contains ULBP and is essentially free of association with other DNA, proteins, or polypeptides, but for the presence of known DNA or proteins that can be removed using a specific antibody, and which substantially purified ULBP proteins retain biological activity. The term "purified ULBP" refers to either the "isolated and purified" form of ULBP or the "substantially purified" form of ULBP, as both are described herein.

The term "active" or "biologically active" as it refers to ULBP protein, means that the ULBP protein is capable of associating with UL16 or being co-immunoprecipitated with UL16 using an antibody to the UL16. Similarly, the association of a ULBP-2 protein with UL16 demonstrates that the ULBP-2 protein is biologically active.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above as well as the Fc moieties described previously.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express ULBP as a secreted polypeptide in order to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

In addition to recombinantly producing ULBP, ULBP can be isolated and purified from cell lines and in particular from Namalwa human B cell lymphoma cells.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

In the methods described above, suitable ULBP-binding polypeptides are anti-ULBP antibodies and other proteins that are capable of high-affinity binding of ULBP. A preferred ULBP-binding protein is an anti-ULBP monoclonal antibody.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Assays

The purified polypeptides of the invention (including proteins, polypeptides, fragments, variants, oligomers, and other forms) may be tested for the ability to bind UL-16 or a ULBP counter-structure molecule in any suitable assay, such as a conventional binding assay. To illustrate, the polypeptide may be labeled with a detectable reagent (e.g., a radionuclide, chromophore, enzyme that catalyzes a colorimetric or fluorometric reaction, and the like). The labeled polypeptide is contacted with cells expressing a ULBP counter-structure molecule. The cells then are washed to remove unbound labeled polypeptide, and the presence of cell-bound label is determined by a suitable technique, chosen according to the nature of the label.

One example of a binding assay procedure is as follows. A recombinant expression vector containing UL16 cDNA is constructed. DNA and amino acid sequence information for UL16 is presented in Kaye et al., J. Virol. 66:6609, 1992. For example, UL16-Fc fuses the extracellular domain of UL16 to the IgG-I Fc (mutein form) as previously described for OX40-Fc (Baum et al., EMBO J. 13:3992–4001, 1994). CV1-EBNA-1 cells in 10 cm$^2$ dishes are transfected with the recombinant expression vector. CV-1/EBNA-1 cells (ATCC CRL 10478) constitutively express EBV nuclear antigen-1 driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

The transfected cells are cultured for 24 hours, and the cells in each dish then are split into a 24-well plate. After culturing an additional 48 hours, the transfected cells (about $4 \times 10^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, a soluble polypeptide/Fc fusion protein made as set forth above. Cells then are washed and incubated with a constant saturating concentration of a $^{125}$I-mouse anti-human IgG in binding medium, with gentle agitation for 1 hour at 37° C. After extensive washing, cells are released via trypsinization.

The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc protein that has bound to the cells. In all assays, non-specific binding of $^{125}$I-antibody is assayed in the absence of the Fc fusion protein/Fc, as well as in the presence of the Fc fusion protein and a 200-fold molar excess of unlabeled mouse anti-human IgG antibody.

Cell-bound $^{125}$I-antibody is quantified on a Packard Auto-gamma counter. Affinity calculations (Scatchard, *Ann. N.Y. Acad. Sci.* 51:660, 1949) are generated on RS/1 (BBN Software, Boston, Mass.) run on a Microvax computer.

Another type of suitable binding assay is a competitive binding assay. To illustrate, biological activity of a variant may be determined by assaying for the variant's ability to compete with the native protein for binding to UL16 or cells expressing a ULBP counterstructure.

Competitive binding assays can be performed by conventional methodology. Reagents that may be employed in competitive binding assays include radiolabeled UL16 and intact cells expressing ULBP (endogenous or recombinant)

on the cell surface. For example, a radiolabeled soluble ULBP fragment can be used to compete with a soluble ULBP variant for binding to cell surface (binding partner). Instead of intact cells, one could substitute a soluble UL16/Fc fusion protein bound to a solid phase through the interaction of Protein A or Protein G (on the solid phase) with the Fc moiety. Chromatography columns that contain Protein A and Protein G include those available from Pharmacia Biotech, Inc., Piscataway, N.J.

Another type of competitive binding assay utilizes radiolabeled soluble UL16 such as a soluble UL16/Fc fusion protein, and intact cells expressing ULBP. Qualitative results can be obtained by competitive autoradiographic plate binding assays, while Scatchard plots (Scatchard, *Ann. N.Y. Acad. Sci.* 51:660, 1949) may be utilized to generate quantitative results.

USE OF ULBP NUCLEIC ACID OR OLIGONUCLEOTIDES

In addition to being used to express polypeptides as described above, the nucleic acids of the invention, including DNA, and oligonucleotides thereof can be used:

- as probes to identify nucleic acid encoding proteins having ULBP activity;
- to identify human chromosome number 6;
- to map genes on human chromosome number 6;
- to identify genes associated with certain diseases, syndromes, or other conditions associated with human chromosome number 6;
- as single-stranded sense or antisense oligonucleotides, to inhibit expression of polypeptide encoded by the ULBP gene;
- to help detect defective genes in an individual; and
- for gene therapy.

Probes

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NO:1, SEQ ID NO:3, and SEQ ID NO:9, from other mammalian species, are contemplated herein, probes based on the DNA sequence of SEQ ID NO:1, SEQ ID NO:3, and SEQ ID NO:9 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Chromosome Mapping

ULBP-1, ULBP-2 and ULBP-3 polypeptides are distantly related to a number of MHC class I proteins, particularly non-classical class I molecules or class I molecules of non-human species. ULBP-1 and ULBP-2 polypeptides contain regions homologous to the α1 and α2 domains of MHC class I proteins. However, they have a different structure from other class 1 molecules in that they lack the alpha-3 domain, which is needed for binding beta-2-microglobulin. In addition, the ULBP-1, ULBP-2 and the ULBP-3 genes map to chromosome 6q20-26, which is distinct from any other MHC class 1 and related genes.

All or a portion of the nucleic acids of SEQ ID NO:1 or SEQ ID NO:3, including oligonucleotides, can be used by those skilled in the art using well-known techniques to identify the human chromosome 6, and the specific locus thereof, that contains the DNA of ULBP family members. Useful techniques include, but are not limited to, using the sequence or portions, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

For example, chromosomes can be mapped by radiation hybridization. PCR is performed using the Whitehead Institute/MrF Center for Genome Research Genebridge4 panel of 93 radiation hybrids. Primers are used which lie within a putative exon of the gene of interest and which amplify a product from human genomic DNA, but do not amplify hamster genomic DNA. The results of the PCRs are converted into a data vector that is submitted to the Whitehead/MIT Radiation Mapping site on the internet. The data is scored and the chromosomal assignment and placement relative to known Sequence Tag Site (STS) markers on the radiation hybrid map is provided.

Identifying Associated Diseases

As set forth below, SEQ ID NO:1 and SEQ ID NO:3 have been mapped to the 6q20-26 region of chromosome 6. That region is associated with specific diseases which include but are not limited to Retinitis pigmentosa-25 (6q14-q21); Diabetes mellitus, insulin-dependent,15 (6q21); Progressive pseudorheumatoid arthropathy of childhood (6q22); Muscular dystrophy, congenital merosin-deficient (6q22-q23); and Cardiomyopathy, dilated, 1F (6q23). Thus, the nucleic acid of SEQ ID NO:1 or SEQ ID NO:3, or a fragment thereof, can be used by one skilled in the art using well-known techniques to analyze abnormalities associated with gene mapping to chromosome 6. This enables one to distinguish conditions in which this marker is rearranged or deleted. In addition, nucleotides of SEQ ID NO:1 or SEQ ID NO:3 or a fragment thereof can be used as a positional marker to map other genes of unknown location.

The DNA may be used in developing treatments for any disorder mediated (directly or indirectly) by defective, or insufficient amounts of, the genes corresponding to the nucleic acids of the invention. Disclosure herein of native nucleotide sequences permits the detection of defective genes, and the replacement thereof with normal genes. Defective genes may be detected in in vitro diagnostic assays, and by comparison of a native nucleotide sequence disclosed herein with that of a gene derived from a person suspected of harboring a defect in this gene.

Sense-Antisense

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of DNA (SEQ ID NO:1, SEQ ID NO:3, or SEQ ID NO:9). Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block or inhibit protein expression by one of several means, including enhanced degradation of the mRNA by RNAseH, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in W091/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, lipofection, $CaPO_4$-mediated DNA transfection, electroporation, or by using gene transfer vectors such as Epstein-Barr virus.

Sense or antisense oligonucleotides are preferably introduced into a cell containing the target nucleic acid sequence by insertion of the sense or antisense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or the double copy vectors designated DCT5A, DCT5B and DCT5C (see PCT Application U.S. Ser. No. 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

USE OF ULBP POLYPEPTIDES AND FRAGMENTED POLYPEPTIDES

Uses include, but are not limited to, the following:

As markers to detect cancer

Enhancement of IFN-γ production and NK cell proliferation

Enhancement of CTL activity

Purifying proteins and measuring activity thereof

Delivery Agents

Therapeutic Agents

Rational Drug Design

Research Reagents

Molecular weight and Isoelectric focusing markers

Controls for peptide fragmentation

Identification of unknown proteins

Preparation of Antibodies

As Markers to Detect Cancer

The ULBP1, ULBP2, and ULBP3 DNAs and polypeptides can be used as markers to detect cancer [hereinafter "ULBP marker"], particularly B cell lymphoma. Generally, markers of cancer represent alterations in the phenotype of a cell that distinguish malignant cells from normal cells. Markers can either be involved in the genesis of a cancer, (such as mutations in oncogenes or tumor suppressor genes), or can be secondary modifications acquired during the progression of the tumor. See, for example, Vincent T. DeVita, Jr., Samuel Hellman, and Steven A. Rosenberg, *Cancer Principles & Practice of Oncology*, 259–284 (5th ed. 1997) (describing the utilization of cancer markers), hereby incorporated by reference in its entirety.

In either case, an ULBP marker facilitates the detection, identification, diagnosis, or prognosis of cancer, particularly B cell lymphoma. The ULBP marker can be used to distinguish malignant from benign neoplasms, as well as distinguish infiltrating reactive processes from neoplastic cells. Furthermore, the ULBP marker can facilitate diagnosis of a tumor by identifying the normal progenitor cell from which a tumor arises by assessing features of tissue differentiation displayed by the tumor. Moreover, the evaluation of cells and tissues for the ULBP marker is useful in the subtyping and staging of tumors, providing critical information concerning prognosis. The ULBP marker can also be used to monitor residual or recurrent disease after treatment. Finally, the ULBP marker can diagnose patients having an inherited predisposition to the development of specific cancer types by identifying a genomic rearrangement in normal tissues. In contrast, non-inherited, or sporadic tumors, will be present with genomic rearrangements of the ULBP gene only in the tumor sample.

Methods of utilizing markers for cancer detection are known to one of ordinary skill in the art. For instance, genomic rearrangement, a hallmark of cancer, can be detected using ULBP DNA. A genomic rearrangement is defined in the instant application as a deletion, an insertion, a translocation, an inversion, an amplification, a duplication, or a point mutation in or proximate to the ULBP gene, including the promoter, the intronic sequence, and the 3' untranslated region (UTR). Methods of detecting a genomic rearrangement in neoplastic cells utilizing the ULBP DNA are known to one of ordinary skill in the art and include, but are not limited to, Southern hybridization, PCR based assays, fluorescence in situ hybridization (FISH), DNA sequence reactions, allelic specific oligonucleotide hybridization, RNase protection, and assays based on conformational differences, such as single-strand conformational polymorphism (SSCP), denaturing gradient gel electrophoresis (DGGE), and enzymes specifically detecting mismatches between sequences, for example, MutS and resolvase. (See, DeVita, pages 263–269, outlining the above well-known procedures used in the detection of cancer by markers.) Genomic rearrangements can also be detected using the ULBP DNA attached to glass chips with hybridization of a sample against the chip.

ULBP DNAs can be used to detect expression of ULBP genes. Many genes that may or may not be involved in the genesis and progression of cancer are either overexpressed, underexpressed, or absent relative to the expression patterns observed in the cell type from which the cancer is believed to have originated. In contrast, the expression levels may be comparable to the normal expression patterns; however, the messenger RNA (mRNA) contains mutations, such as stop, point, or alternative splicing mutations, not found in the wild type gene. The detection of these altered expression patterns and mRNA species in a cancer cell can be used as a marker of that particular cancer type.

ULBP polynucleotides can be used to detect expression patterns and mRNA species in a cancer cell, particularly B cell lymphoma. Again, one skilled in the art would know how to modify known methods to detect expression patterns and mRNA species of ULBP genes. One method involves performing a Northern hybridization by isolating either mRNA or total RNA from a cancer cell and probing with ULBP nucleotides. Detection can also be performed by a reverse-transcriptase polymerase chain reaction (RT-PCR) based assay, or a combination of RT-PCR and Southern hybridization. Furthermore, mutations in the mRNA species can be detected by the above procedures for detecting genomic rearrangements.

In situ hybridization (ISH) is yet another well-known method that can be used in the instant invention to detect ULBP expression and mRNA species. (See, DeVita, page 267.) For example, paraffin embedded tissues obtained from a patient can be screened using labeled ULBP nucleotide complementary to the mRNA, allowing for the comparison of expression patterns in neoplastic cells adjacent to normal tissues. Thus, by disclosing the sequences of the ULBPs of the present invention, one of ordinary skill in the art can easily modify known methods of utilizing markers to detect mRNA species in normal and cancer cells.

Not only can ULBP nucleotides be used as markers to detect cancer, but also assays utilizing ULBP polypeptides can be designed to detect cancer. In one embodiment, isolated and purified ULBP polypeptides can be incubated with lymphoma cells under conditions that allow binding of the ULBP polypeptide to lymphoma cells. Unbound ULBP polypeptide can be removed using a washing step, and bound ULBP polypeptide can be detected using an anti-ULBP monoclonal antibody. (See Meyers et al., *Leuk. and Lymph.* 18:119–122).

In another embodiment, assays utilizing antibodies prepared from ULBP polypeptides can be designed to detect cancer. (See, DeVita, pages 260–262.) For example, antibodies raised against ULBP polypeptides can be used in immunohistologic examinations to distinguish benign from malignant proliferations. These immunohistologic examinations may detect overproduction, underproduction, or miscompartmentalization of the ULBP protein in cancer cells relative to the normal cells of origin. Evidence of an alteration in the production of the wild-type ULBP protein can be a marker associated with a more malignant or advanced stage of cancer.

Similarly, abnormally produced ULBP proteins can be detected by antibodies directed against the ULBP protein in samples taken from bodily fluids. For instance, abnormally produced ULBP protein may fail to remain in the cellular membrane, and instead be secreted by the cell into the patient's blood stream. Blood samples taken from a patient are then analyzed using ULBP antibodies to determine the presence of abnormal ULBP protein in the blood by a flow cytometer. The presence of abnormal ULBP protein in the blood stream may help monitor therapy and detect progression or relapse in patients with cancer, particularly B cell lymphoma.

Enhancement of IFNγ Production and NK Cell Proliferation

ULBP polypeptides have been used to enhance IFN-γ production and NK cell proliferation in a dose-dependent manner. Therefore, ULBP polypeptides can be used in methods to enhance IFN-γ production and NK cell proliferation by incubating ULBP polypeptides with NK cells, for example, as described in Example 5. The skilled artisan recognizes that ULBP polypeptides can be used to enhance IFN-γ production and NK cell proliferation both in vitro and in vivo. The skilled artisan further appreciates that the enhancement of IFN-γ production and NK cell proliferation by ULBP polypeptides can modulate an immune response, for example, against viruses, bacteria, parasites, and tumors.

ULBP polypeptides have been used to enhance CTL activity in a dose-dependent manner. Therefore, ULBP polypeptides can be used in methods to enhance CTL activity by incubating ULBP polypeptides with CTLs, for example, as described in Example 6. The skilled artisan recognizes that ULBP polypeptides can be used to enhance CTL activity both in vitro and in vivo. The skilled artisan further appreciates that the enhancement of CTL activity by ULBP polypeptides can modulate an immune response, for example, against viruses, bacteria, and tumors.

Anti-viral and Anti-tumor Therapeutics

The polypeptide of the present invention also find utility as therapeutic agents for the treatment of tumors and viral infections. Accordingly, the present invention encompasses methods for inhibiting or halting a tumor growth by administering to an individual inflicted with a tumor, a ULBP polypeptide or a fragment of a ULBP polypeptide that binds to NK cells. Additionally, the present invention encompasses methods for treating viral infection by administering to an individual inflicted with an invention a ULBP polypeptide of a fragment of a ULBP polypeptide that binds to NK cells.

In NK cell culture systems in which ULBP proteins and IL-12 were shown to synergize strongly in inducing interferon-gamma production from NK cells pretreated with IL-15, (see Example 5) it was also shown that the ULBP proteins upregulate mRNA levels for chemokines. In particular, the chemokines I-309 and lymphotactin were shown to be upregulated by the ULBP proteins. Additionally, in the same NK cell culture system, certain cytokines that are known to be markers of NK cell activation, including GM-CSF, lymphotoxin-alpha and TNF-alpha are upregulated. As discussed above, NK cells are capable of exerting a cytotoxic effect by lysing a variety of cell types. Thus, a host system's ability to activate NK cells and target the activated NK cell to an infected cell or tumor cell is important in fighting infection and tumors.

As described and demonstrated in Example 7, the ULBP proteins, as well as MICA bind to NKG2D/Dap10, an antigen expressed by NK cells. The ability of the ULBP proteins to synergize in the production of key cytokines indicates that the ULBP proteins can activate NK cell cytolytic function. Accordingly, ULBP proteins find utility as an anti-viral and anti tumor therapeutic. Moreover, bifunctional molecules or multifunctional molecules, that are able to bind and activate NK cells and also bind tumor cells are useful in accordance with the present invention. Suitable bifunctional or multifunctional molecules may be molecules that include at least one ULBP protein, or NK cell binding fragment of a ULBP protein, and, a single chain antibody against a tumor. It can be appreciated that such a therapeutic is capable of binding to and activating NK cells and then targeting tumor cells for lysing by the NK cell.

Purification Reagents

Each of the polypeptides of the invention finds use as a protein purification reagent. The polypeptides may be attached to a solid support material and used to purify ULBP counter-structure molecules by affinity chromatography. In particular embodiments, a polypeptide (in any form described herein that is capable of binding ULBP counter-structure molecules) is attached to a solid support by conventional procedures. As one example, chromatography columns containing functional groups that will react with functional groups on amino acid side chains of proteins are available (Pharmacia Biotech, Inc., Piscataway, N.J.). In an alternative, a polypeptide/Fc protein (as discussed above) is attached to Protein A- or Protein G-containing chromatography columns through interaction with the Fc moiety.

The polypeptide also finds use in purifying or identifying cells that express ULBP counter-structure molecules on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing ULBP counter-structure molecule-expressing cells are contacted with the solid phase having the polypeptides thereon. Cells expressing ULBP counter-structure molecules on the cell surface bind to the fixed polypeptides, and unbound cells then are washed away.

Alternatively, the polypeptides can be conjugated to a detectable moiety, then incubated with cells to be tested for ULBP counter-structure molecules expression. After incubation, unbound labeled matter is removed and the presence or absence of the detectable moiety on the cells is determined.

In a further alternative, mixtures of cells suspected of containing cells expressing ULBP counter-structure molecules are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.*, 10D:239, 1986). Washing to remove unbound material, and the release of the bound cells, are performed using conventional methods.

Measuring Activity

Polypeptides also find use in measuring the biological activity of ULBP counter-structure molecules in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of a ULBP counter-structure molecule that has been stored at different temperatures, or produced in different cell types. The proteins also may be used to determine whether biological activity is retained after modification of a ULBP counter-structure molecule (e.g., chemical modification, truncation, mutation, etc.). The binding affinity of the modified ULBP counter-structure molecule is compared to that of an unmodified ULBP counter-structure molecules to detect any adverse impact of the modifications on biological activity of ULBP counter-structure molecules. The biological activity of a ULBP counter-structure molecule thus can be ascertained before it is used in a research study, for example.

Delivery Agents

The polypeptides can be used to deliver diagnostic or therapeutic agents to such cells or cell types found to express ULBP counterstructure molecules on the cell surface in in vitro or in vivo procedures. For example, ULBP1-Fc binds to anaplastic lymphomas. Therefore, ULBP-1 polypeptide can be attached to a toxin to bind to lymphoma cells and specifically kill these cells. The methodology can be similar to the successful use of an anti-CD72 immunotoxin to treat therapy-refractory B-lineage acute lymphoblastic leukemia in SCID mice (Meyers et al., *Leuk. and Lymph.* 18:119–122).

In addition, ULBP1-Fc and ULBP2-Fc bind to activated T cells more strongly than resting T cells. Therefore, when attached to toxins or made radioactive, they can be used to kill activated T cells in diseases where T cells are overactive (autoimmunity), such as lupus, multiple sclerosis, rheumatoid arthritis, psoriasis, graft rejection, and graft versus host disease. Since they also bind to NK cells, they can be used to kill NK cells, which would help in treating graft rejection.

Detectable (diagnostic) and therapeutic agents that may be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudoinoias aerugiinosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the polypeptide by any suitable conventional procedure. The polypeptide comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to polypeptides by using a suitable bifunctional chelating agent, for example.

Conjugates comprising polypeptides and a suitable diagnostic or therapeutic agent (preferably covalently linked) are thus prepared. The conjugates are administered or otherwise employed in an amount appropriate for the particular application.

Therapeutic Agents

Polypeptides of the invention may be used in developing treatments for any disorder mediated (directly or indirectly) by defective, or insufficient amounts of the polypeptides. These polypeptides may be administered to a mammal afflicted with such a disorder.

The polypeptides may also be employed in inhibiting a biological activity of ULBP counterstructure molecules, in in vitro or in vivo procedures. For example, a purified polypeptide may be used to inhibit binding of ULBP counter-structure molecules to endogenous cell surface molecules. Biological effects that result from the binding of ULBP counter-structure molecules to endogenous receptors thus are inhibited.

ULBP polypeptides may be administered to a mammal to treat a ULBP counter-structure molecule-mediated disorder. Such ULBP counter-structure molecules-mediated disorders include conditions caused (directly or indirectly) or exacerbated by ULBP counter-structure molecules.

Compositions of the present invention may contain a polypeptide in any form described herein, such as native proteins, variants, derivatives, oligomers, and biologically active fragments. In particular embodiments, the composition comprises a soluble polypeptide or an oligomer comprising soluble ULBP polypeptides.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences*, 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Compositions comprising nucleic acids in physiologically acceptable formulations are also contemplated. DNA may be formulated for injection, for example.

Rational Drug Design

In addition, ULBP polypeptides can also be used for structure-based design of ULBP inhibitors. Such structure-based design is also known as "rational drug design." The ULBP polypeptides can be three dimensionally analyzed by, for example, X-ray crystallography, nuclear magnetic resonance, or homology modeling, all of which are well known methods. The use of ULBP structural information in molecular modeling software systems to assist in inhibitor design and inhibitor-ULBP interaction is also encompassed by the invention. Such computer-assisted modeling and drug design may utilize information such as chemical conformational analysis, electrostatic potential of the molecules, protein folding, etc. For example, most of the design of class-specific inhibitors of metalloproteases has focused on attempts to chelate or bind the catalytic zinc atom. Synthetic inhibitors are usually designed to contain a negatively charged moiety to which is attached a series of other groups designed to fit the specificity pockets of the particular protease. A particular method of the invention comprises analyzing the three dimensional structure of ULBP for likely binding sites of substrates, synthesizing a new molecule that incorporates a predictive reactive site, and assaying the new molecule as described above.

Research Reagents

Another use of the polypeptide of the present invention is as a research tool for studying the biological effects that result from inhibiting ULBP /ULBP counter-structure interactions on different cell types. Polypeptides also may be employed in in vitro assays for detecting ULBP counter-structure molecules or ULBP polypeptides or the interactions thereof.

ULBP may also be used as a reagent to identify (a) the proteins to which it binds, and which are involved in ULBP signaling, and (b) other proteins with which it might interact which would be involved in signal transduction pathways. These other proteins would then be useful tools to search for other inhibitors of signaling. ULBP could be used by coupling recombinant protein to an affinity matrix, or by using it as a bait in the 2-hybrid system.

The interaction between ULBP polypeptide and its counter-structure enables screening for small molecules that interfere with the ULBP polypeptide/ULBP counter-structure association and inhibit activity of ULBP polypeptide or its counter-structure. For example, the yeast two-hybrid system developed at SUNY (described in U.S. Pat. No. 5,283,173 to Fields et al.) may be used to screen for inhibitors of ULBP as follows. ULBP polypeptide and its counter-structure, or portions thereof responsible for their interaction, may be fused to the Gal 4 DNA binding domain and Gal 4 transcriptional activation domain, respectively, and introduced into a strain that depends on Gal 4 activity for growth on plates lacking histidine. Compounds that prevent growth may be screened in order to identify ULBP inhibitors. Alternatively, the screen may be modified so that ULBP polypeptide/ULBP polypeptide counter-structure interaction inhibits growth, so that inhibition of the interaction allows growth to occur.

Another, in vitro, approach to screening for ULBP inhibition would be to immobilize one of the components (either ULBP polypeptide or its counter-structure) in wells of a microtiter plate, and to couple an easily detected indicator to the other component. An inhibitor of the interaction is identified by the absence of the detectable indicator from the well.

In addition, ULBP polypeptides according to the invention are useful for the structure-based design of an ULBP inhibitor. Such a design would comprise the steps of determining the three-dimensional structure of the ULBP polypeptide, analyzing the three-dimensional structure for the likely binding sites of substrates, synthesizing a molecule that incorporates a predictive reactive site, and determining the inhibiting activity of the molecule.

ULBP DNA, ULBP polypeptides, and antibodies against ULBP polypeptides can be used as reagents in a variety of research protocols. A sample of such research protocols are given in Sambrook et al. *Molecular Cloning: A Laboratory Manual*, 2 ed. Vol. 1–3, Cold Spring Harbor Laboratory Press, (1989). For example, these reagents can serve as markers for cell specific or tissue specific expression of RNA or proteins. Similarly, these reagents can be used to investigate constituitive and transient expression of ULBP RNA or polypeptides. ULBP DNA can be used to determine the chromosomal location of ULBP DNA and to map genes in relation to this chromosomal location. ULBP DNA can also be used to examine genetic heterogeneity and heredity, through the use of techniques such as genetic fingerprinting, as well as to identify risks associated with genetic disorders. ULBP DNA can be further used to identify additional genes related to ULBP DNA and to establish evolutionary trees based on the comparison of sequences. ULBP DNA and polypeptides can be used to select for those genes or proteins that are homologous to ULBP DNA or polypeptides through positive screening procedures, such as Southern blotting and immunoblotting, and through negative screening procedures, such as subtraction.

Molecular Weight, Isoelectric Point Markers

The polypeptides of the present invention can be subjected to fragmentation into smaller peptides by chemical and enzymatic means, and the peptide fragments so produced can be used in the analysis of other proteins or polypeptides. For example, such peptide fragments can be used as peptide molecular weight markers, peptide isoelectric point markers, or in the analysis of the degree of peptide fragmentation. Thus, the invention also includes these polypeptides and peptide fragments, as well as kits to aid in the determination of the apparent molecular weight and isoelectric point of an unknown protein and kits to assess the degree of fragmentation of an unknown protein.

Although all methods of fragmentation are encompassed by the invention, chemical fragmentation is a preferred embodiment, and includes the use of cyanogen bromide to cleave under neutral or acidic conditions such that specific cleavage occurs at methionine residues (E. Gross, *Methods in Enz*. 11:238–255, 1967). This can further include additional steps, such as a carboxymethylation step to convert cysteine residues to an unreactive species.

Enzymatic fragmentation is another preferred embodiment, and includes the use of a protease such as Asparaginylendo-peptidase, Arginylendo-peptidase, Achromobacter protease I, Trypsin, *Staphlococcus aureus* V8 protease, Endoproteinase Asp-N, or Endoproteinase Lys-C under conventional conditions to result in cleavage at specific amino acid residues. Asparaginylendo-peptidase can cleave specifically on the carboxyl side of the asparagine residues present within the polypeptides of the invention. Arginylendo-peptidase can cleave specifically on the carboxyl side of the arginine residues present within these polypeptides. Achromobacter protease I can cleave specifically on the carboxyl side of the lysine residues present within the polypeptides (Sakiyama and Nakat, U.S. Pat. No. 5,248,599; T. Masaki et al., *Biochim. Biophys. Acta* 660:44–50, 1981; T. Masaki et al., *Biochim. Biophys. Acta* 660:51–55, 1981). Trypsin can cleave specifically on the carboxyl side of the arginine and lysine residues present within polypeptides of the invention. Enzymatic fragmentation may also occur with a protease that cleaves at multiple amino acid residues. For example, *Staphlococcus aureus* V8 protease can cleave specifically on the carboxyl side of the aspartic and glutamic acid residues present within polypeptides (D. W. Cleveland, *J. Biol. Chem*. 3:1102–1106, 1977). Endoproteinase Asp-N can cleave specifically on the amino side of the asparagine residues present within polypeptides. Endoproteinase Lys-C can cleave specifically on the carboxyl side of the lysine residues present within polypeptides of the invention. Other enzymatic and chemical treatments can likewise be used to specifically fragment these polypeptides into a unique set of specific peptides.

Of course, the peptides and fragments of the polypeptides of the invention can also be produced by conventional recombinant processes and synthetic processes well known in the art. With regard to recombinant processes, the polypeptides and peptide fragments encompassed by invention can have variable molecular weights, depending upon the host cell in which they are expressed. Glycosylation of polypeptides and peptide fragments of the invention in various cell types can result in variations of the molecular weight of these pieces, depending upon the extent of modification. The size of these pieces can be most heterogeneous with fragments of polypeptide derived from the extracellular portion of the polypeptide. Consistent polypeptides and peptide fragments can be obtained by using polypeptides derived entirely from the transmembrane and cytoplasmic regions, pretreating with N-glycanase to remove glycosylation, or expressing the polypeptides in bacterial hosts.

The molecular weight of these polypeptides can also be varied by fusing additional peptide sequences to both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein. In addition, fusions of additional peptide sequences at the amino and carboxyl terminal ends of polypeptides of the invention will alter some, but usually not all, of the fragmented peptides of the polypeptides generated by enzymatic or chemical treatment. Of course, mutations can be introduced into polypeptides of the invention using routine and known techniques of molecular biology. For example, a mutation can be designed so as to eliminate a site of proteolytic cleavage by a specific enzyme or a site of cleavage by a specific chemically induced fragmentation procedure. The elimination of the site will alter the peptide fingerprint of polypeptides of the invention upon fragmentation with the specific enzyme or chemical procedure.

The polypeptides and the resultant fragmented peptides can be analyzed by methods including sedimentation, electrophoresis, chromatography, and mass spectrometry to determine their molecular weights. Because the unique amino acid sequence of each piece specifies a molecular weight, these pieces can thereafter serve as molecular weight markers using such analysis techniques to assist in the determination of the molecular weight of an unknown protein, polypeptides or fragments thereof. The molecular weight markers of the invention serve particularly well as molecular weight markers for the estimation of the apparent molecular weight of proteins that have similar apparent molecular weights and, consequently, allow increased accuracy in the determination of apparent molecular weight of proteins.

When the invention relates to the use of ULBP polypeptide fragments and fragmented peptide molecular weight markers, those markers are preferably at least 10 amino acids in size. More preferably, these fragmented peptide molecular weight markers are between 10 and 100 amino acids in size. Even more preferable are fragmented peptide molecular weight markers between 10 and 50 amino acids in size and especially between 10 and 35 amino acids in size. Most preferable are fragmented peptide molecular weight markers between 10 and 20 amino acids in size.

Among the methods for determining molecular weight are sedimentation, gel electrophoresis, chromatography, and mass spectrometry. A particularly preferred embodiment is denaturing polyacrylamide gel electrophoresis (U. K. Laemmli, *Nature* 227:680–685, 1970). Conventionally, the method uses two separate lanes of a gel containing sodium dodecyl sulfate and a concentration of acrylamide between 6–20%. The ability to simultaneously resolve the marker and the sample under identical conditions allows for increased accuracy. It is understood, of course, that many different techniques can be used for the determination of the molecular weight of an unknown protein using polypeptides of the invention, and that this embodiment in no way limits the scope of the invention.

Each unglycosylated polypeptide or fragment thereof has a pI that is intrinsically determined by its unique amino acid sequence (which pI can be estimated by the skilled artisan using any of the computer programs designed to predict pI values currently available, calculated using any well-known amino acid pKa table, or measured empirically). Therefore these polypeptides and fragments thereof can serve as specific markers to assist in the determination of the isoelectric point of an unknown protein, polypeptide, or fragmented peptide using techniques such as isoelectric focusing. These polypeptide or fragmented peptide markers serve particularly well for the estimation of apparent isoelectric points of unknown proteins that have apparent isoelectric points close to that of the polypeptide or fragmented peptide markers of the invention.

The technique of isoelectric focusing can be further combined with other techniques such as gel electrophoresis to simultaneously separate a protein on the basis of molecular weight and charge. The ability to simultaneously resolve these polypeptide or fragmented peptide markers and the unknown protein under identical conditions allows for increased accuracy in the determination of the apparent isoelectric point of the unknown protein. This is of particular interest in techniques, such as two dimensional electrophoresis (T. D. Brock and M. T. Madigan, *Biology of Microorganisms* 76–77 (Prentice Hall, 6d ed. 1991)), where the nature of the procedure dictates that any markers should be resolved simultaneously with the unknown protein. In addition, with such methods, these polypeptides and fragmented peptides thereof can assist in the determination of both the isoelectric point and molecular weight of an unknown protein or fragmented peptide.

Polypeptides and fragmented peptides can be visualized using two different methods that allow a discrimination between the unknown protein and the molecular weight markers. In one embodiment, the polypeptide and fragmented peptide molecular weight markers of the invention can be visualized using antibodies generated against these markers and conventional immunoblotting techniques. This detection is performed under conventional conditions that do not result in the detection of the unknown protein. It is understood that it may not be possible to generate antibodies against all polypeptide fragments of the invention, since small peptides may not contain immunogenic epitopes. It is further understood that not all antibodies will work in this assay; however, those antibodies which are able to bind polypeptides and fragments of the invention can be readily determined using conventional techniques.

The unknown protein is also visualized by using a conventional staining procedure. The molar excess of unknown protein to polypeptide or fragmented peptide molecular weight markers of the invention is such that the conventional staining procedure predominantly detects the unknown protein. The level of these polypeptide or fragmented peptide molecular weight markers is such as to allow little or no detection of these markers by the conventional staining method. The preferred molar excess of unknown protein to polypeptide molecular weight markers of the invention is between 2 and 100,000 fold. More preferably, the preferred molar excess of unknown protein to these polypeptide molecular weight markers is between 10 and 10,000 fold and especially between 100 and 1,000 fold.

It is understood of course that many techniques can be used for the determination and detection of molecular weight and isoelectric point of an unknown protein, polypeptides, and fragmented peptides thereof using these polypeptide molecular weight markers and peptide fragments thereof and that these embodiments in no way limit the scope of the invention.

In another embodiment, the analysis of the progressive fragmentation of the polypeptides of the invention into specific peptides (D. W. Cleveland et al., *J. Biol. Chem.* 252:1102–1106, 1977), such as by altering the time or temperature of the fragmentation reaction, can be used as a control for the extent of cleavage of an unknown protein. For example, cleavage of the same amount of polypeptide and unknown protein under identical conditions can allow for a direct comparison of the extent of fragmentation. Conditions that result in the complete fragmentation of the polypeptide can also result in complete fragmentation of the unknown protein.

As to the specific use of the polypeptides and fragmented peptides of the invention as molecular weight markers, the fragmentation of the polypeptide of SEQ ID NO:2, SEQ ID NO:4, or SEQ ID NO:10 with cyanogen bromide generates a unique set of fragmented peptide molecular weight markers with unique molecular weights. The distribution of methionine residues determines the number of amino acids in each peptide and the unique amino acid composition of each peptide determines its molecular weight.

In addition, the preferred purified polypeptide of the invention has a calculated molecular weight of approximately 31,000 Daltons in the absence of glycosylation.

Where an intact protein is used, the use of these polypeptide molecular weight markers allows increased accuracy in the determination of apparent molecular weight of proteins that have apparent molecular weights close to 31,000 Daltons. Where fragments are used, there is increased accuracy in determining molecular weight over the range of the molecular weights of the fragment.

Finally, as to the kits that are encompassed by the invention, the constituents of such kits can be varied, but typically contain the polypeptide and fragmented peptide molecular weight markers. Also, such kits can contain the polypeptides wherein a site necessary for fragmentation has been removed. Furthermore, the kits can contain reagents for the specific cleavage of the polypeptide and the unknown protein by chemical or enzymatic cleavage. Kits can further contain antibodies directed against polypeptides or fragments thereof of the invention.

Identification of Unknown Proteins

As set forth above, a polypeptide or peptide fingerprint can be entered into or compared to a database of known proteins to assist in the identification of the unknown protein using mass spectrometry (W. J. Henzel et al., Proc. Natl. Acad. Sci. USA: 90:5011–5015, 1993; D. Fenyo et al., Electrophoresis 19:998–1005, 1998). A variety of computer software programs to facilitate these comparisons are accessible via the Internet, such as Protein Prospector, MultiIdent, PeptideSearch, and ProFound. These programs allow the user to specify the cleavage agent and the molecular weights of the fragmented peptides within a designated tolerance. The programs compare observed molecular weights to predicted peptide molecular weights derived from sequence databases to assist in determining the identity of the unknown protein.

In addition, a polypeptide or peptide digest can be sequenced using tandem mass spectrometry (MS/MS) and the resulting sequence searched against databases (J. K. Eng, et al., J. Am. Soc. Mass Spec. 5:976–989 (1994); M. Mann and M. Wilm, Anal. Chem. 66:43904399 (1994); J. A. Taylor and R. S. Johnson, Rapid Comm. Mass Spec. 11: 1067–1075 (1997)). Searching programs that can be used in this process exist on the Internet, such as Lutefisk 97, and the Protein Prospector, Peptide Search and ProFound programs described above.

Therefore, adding the sequence of a gene and its predicted protein sequence and peptide fragments to a sequence database can aid in the identification of unknown proteins using mass spectrometry.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as immunogens in producing antibodies immunoreactive therewith.

In another aspect of the invention, ULBP1, ULBP2, ULBP3 and peptides based on the amino acid sequence of these ULBP proteins, can be utilized to prepare antibodies that specifically bind to ULBP1, ULBP2, and ULBP3, respectively. Specific examples of such antibody preparations are described in Examples 3 and 4 herein. Example 9 describes binding experiments that substantiate the ability of certain antibodies to block binding of proteins to which they are specific to cell transfected with a protein expressed on NK cells. The term "antibodies" is meant to include polyclonal antibodies, monoclonal antibodies, fragments thereof, such as F(ab')2 and Fab fragments, as well as any recombinantly produced binding partners. Antibodies are defined to be specifically binding if they bind ULBP polypeptide with a $K_a$ of greater than or equal to about $10^7$ $M^{-1}$ Affinities of binding partners or antibodies can be readily determined using conventional techniques, for example those described by Scatchard et al., *Anal. N.Y Acad. Sci.*, 51:660 (1949).

Polyclonal antibodies can be readily generated from a variety of sources, for example, horses, cows, goats, sheep, dogs, chickens, rabbits, mice, or rats, using procedures that are well known in the art. In general, purified ULBP or a peptide based on the amino acid sequence of ULBP polypeptide that is appropriately conjugated is administered to the host animal typically through parenteral injection. The immunogenicity of ULBP polypeptide can be enhanced through the use of an adjuvant, for example, Freund's complete or incomplete adjuvant. Following booster immunizations, small samples of serum are collected and tested for reactivity to ULBP polypeptide. Examples of various assays useful for such determination include those described in *Antibodies: A Laboratory Manual*, Harlow and Lane (eds.), Cold Spring Harbor Laboratory Press, 1988; as well as procedures, such as countercurrent immunoelectrophoresis (CIEP), radioimmunoassay, radioimmunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. RE 32,011, 4,902,614, 4,543, 439, and 4,411,993; Monoclonal Antibodies, Hybridomas: *A New Dimension in Biological Analyses*, Plenum Press, Kennett, McKearn, and Bechtol (eds.), 1980. Briefly, the host animals, such as mice, are injected intraperitoneally at least once and preferably at least twice at about 3 week intervals with isolated and purified ULBP or conjugated ULBP peptide, optionally in the presence of adjuvant. Mouse sera are then assayed by conventional dot blot technique or antibody capture (ABC) to determine which animal is best to fuse. Approximately two to three weeks later, the mice are given an intravenous boost of ULBP or conjugated ULBP peptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as $^{125}$I-ULBP, is added to each well followed by incubation. Positive wells can be subsequently detected by autoradiography. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", *Strategies in Molecular Biology* 3:1–9 (1990), which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7:394 (1989).

Antigen-binding fragments of such antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

In one embodiment, the antibodies are specific for the polypeptides of the present invention, and do not cross-react with other proteins. Screening procedures by which such antibodies may be identified are well known, and may involve immunoaffinity chromatography, for example.

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, *Monoclonal Antibodies, Hybridomas: A New Dimension in Biological Analyses*, Kennet et al. (eds.), Plenum Press, New York (1980); and Antibodies: *A Laboratory Manual*, Harlow and Land (eds.), Cold Spring Harbor Laboratory Press, Cold Spring Harbor, N.Y., (1988).

Uses Thereof

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Those antibodies that additionally can block binding of the polypeptides of the invention to ULBP counter-structure molecules may be used to inhibit a biological activity that results from such binding. For example, NK cell function that results from binding of ULBP1, ULBP2, or ULBP3 binding to NK cells can be inhibited using antibodies that block binding of ULBP1, ULBP2 or ULBP3 to NK cells. Such blocking antibodies may be identified using any suitable assay procedure, such as by testing antibodies for the ability to inhibit binding of ULBP polypeptides to certain cells expressing ULBP counter-structure molecules. Example 9 describes activities associated with some of such antibodies. Examples of such cells are NK cells and cytotoxic T lymphocytes. Alternatively, blocking antibodies may be identified in assays for the ability to inhibit a biological effect that results from binding of ULBP counter-structure molecules to target cells. Antibodies may be assayed for the ability to inhibit ULBP counter-structure molecules-mediated lysis of cells, for example.

Such an antibody may be employed in an in vitro procedure, or administered ill vivo to inhibit a biological activity mediated by the entity that generated the antibody. Disorders caused or exacerbated (directly or indirectly) by the interaction of ULBP1, ULBP2, or ULBP3 counter-structure molecules with cell surface (binding partner) receptor thus may be treated. A therapeutic method involves in vivo administration of a blocking antibody to a mammal in an amount effective in inhibiting a ULBP counter-structure molecule-mediated biological activity. Monoclonal antibodies are generally preferred for use in such therapeutic methods. In one embodiment, an antigen-binding antibody fragment is employed.

Antibodies may be screened for agonistic (i.e., ligand-mimicking) properties. Such antibodies, upon binding to cell surface ULBP1, ULBP2, or ULBP3 polypeptides, induce biological effects (e.g., transduction of biological signals) similar to the biological effects induced when ULBP counter-structure molecules binds to cell surface ULBP polypeptides.

Compositions comprising an antibody that is directed against ULBP polypeptides, and a physiologically acceptable diluent, excipient, or carrier, are provided herein. Suitable compounds of such compositions are as described above for compositions containing ULBP polypeptides.

Also provided herein are conjugates comprising a detectable (e.g., diagnostic) or therapeutic agent, attached to the antibody. Examples of such agents are presented above. The conjugates find use in in vitro or in vivo procedures, The references cited herein are incorporated by reference herein in their entirety.

The embodiments within the specification and the following Examples provide an illustration of embodiments of the invention and should not be construed to limit the scope of the invention. The skilled artisan recognizes many other embodiments are encompassed by the claimed invention. In the following Examples, all methods described are conventional unless otherwise specified.

EXAMPLE 1

Recombinant Expression of Human ULBP-1

A human ULBP1-Fc construct was generated in the following manner. ULBP-1 DNA encoding the extracellular domain of human ULBP-1 polypeptide(residues 1–218) was generated by PCR using an upstream p rim e r containing an XhoI site (5 '-GCAACTCGAGAGCTCCAGGTCTACAAT GGCAG-3') and a downstream primer containing a BglII site (5 '-GATGAGATCToGGTTGGGTTGTGCCTGG GGCCAG-3'). The human ULBP-1 DNA fragment was cloned in frame into the pDC409 vector containing a 5' SalI site and the human immunoglobulin Fc region mutein (described in EMBO J. 13:3992, 1994) preceded by a BglII site.

The human ULBP1-Fc fusion polypeptide was produced and purified as described in Fanslow et al., *J. Immunol.* 149:655, 1992, which is incorporated by reference.

The human ULBP1-LZ fusion polypeptide was produced using the expression vectors, transfection, and cell culture procedures used for the ULBP1-Fc polypeptide. For purification, the poly His tag is used to bind the recombinant protein to Nickel-NTA resin (manufactured by Qiagen) according to the manufacturer's instructions. The resin is washed with 30 column volumes of 20 mM NaPO4 pH 7.4+300 mM NaCl+5 mM Imidazole. The recombinant protein is then eluted using increasing concentrations of Imidazole. Initially a gradient of 5–20 mM Imidazole 20 mM NaPO4 pH 7.4+300 mM NaCl is used, followed by 20 mM Imidazole 20 mM NaPO4 pH 7.4+300 mM NaCl, followed by a gradient of 20–100 mM Imidazole 20 mM NaPO4 pH 7.4+300 mM NaCl, followed by 100 mM Imidazole 20 mM NaPO4 pH 7.4+300 mM NaCl, followed by 500 mM Imidazole 20 mM NaPO4 pH 7.4+300 mM NaCl. Fractions are collected and analysed by SDS-PAGE to identify those containing the recombinant protein.

EXAMPLE 2

Recombinant Expression of Human ULBP-2

A human ULBP2-Fc construct was generated in the following manner. ULBP2-DNA encoding the extracellular domain of human ULBP-2 polypeptide(residues 1–223) was generated by PCR using an upstream primer containing an XhoI site (5'-GATTCTCGAGTCCTTAATGGCAGCAGCC-3') and a downstream primer containing a BamHI site (5'-ACAAGGATCCCCTGAGTTGGGTTGTGCC-3). The human ULBP-1 DNA fragment was cloned in frame into the pDC409 vector containing a 5' SalI site and the human immunoglobulin Fc region mutein (described in EMBO J. 13:3992, 1994) preceded by a BglII site.

The human ULBP2-Fc fusion polypeptide was produced and purified as described in Fanslow et al., *J. Immunol.* 149:655, 1992, which is incorporated by reference.

The human ULBP2-LZ fusion polypeptide was produced and purified as described above for the ULBP1-LZ fusion polypeptide.

EXAMPLE 3

Preparation of Antibodies Against ULBP-1

Monoclonal antibodies were generated against ULBP-1. Balb/c mice were immunized with 10 μg of ULBP1-Fc (1 mg/ml stock, batch #1) in Titermax adjuvant (CytRx Corp., Norcross, Ga.). The animals were boosted 2 weeks later with 10 μg of the same protein in Freunds Complete Adjuvant (Sigma). Twelve weeks after second immunization, one mouse was boosted intravenously with 10 μg of ULBP1-Fc (Batch #3) in saline. Four days later, the mouse was sacrificed and spleen and lymph nodes were fused with NS1 myelomas with 50% PEG/DMSO solution. The fused cells were placed into 96 well plates (Costar) with HAT (Sigma) selective media. Hybridoma supernatants were screened for antibody production by antibody capture assay (ABC). Briefly, 96 well plates (Nunc) were coated overnight with goat-anti-mouse IgG Fc specific (Pierce), then washed 4 times with PBS. Supernatants were incubated 1 hour at room temperature then washed 5 times with PBS. ULBP1-Fc was added to each well and incubated 1 hour at room temperature followed by 5 washes of PBS. Goat-anti-human Ig Fc fragment specific (Jackson) was added and incubated for 1 hour followed by 5 washes with PBS. The plates were developed with TMB substrate (KPL) and read on a plate reader at 650 nm. Positive wells were subsequently screened against irrelevant Fc protein to remove antibodies reactive to human Fc. They were also screened by flow cytometry for binding to ULBP-1 transfected CV-1 cells. Positive hybridomas were cloned by titration and limiting dilution methods and grown in bulk culture. Supernatants were purified over a Protein A column (Bio-Rad) and stored at −20° C.

EXAMPLE 4

Preparation of Antibodies Against ULBP-2

Monoclonal antibodies were generated against ULBP-2. Balbic mice were immunized with 10 μg of ULBP2-Fc in Titermax adjuvant (CytRX Corp., Norcross, Ga.). The animals were boosted 2 weeks later with 10 μg of the same protein in Freunds Complete Adjuvant (Sigma). Eight weeks after second immunization, one mouse was boosted intravenously with 6 μg of ULBP2-Fc in saline. Four days later the mouse was sacrificed and spleen and lymph nodes were fused with NS1 myelomas with 50% PEG/DMSO solution. The fused cells were plated into 96 well plates (Costar) with HAT (Sigma) selective media. Hybridoma supernatants were screened for antibody production by antibody capture assay (ABC). Briefly, 96 well plates (Nunc) were coated overnight with goat-anti-mouse IgG Fc specific (Pierce), then washed 4 times with PBS. Supernatants were incubated 1 hour at room temperature then washed 5 times with PBS. ULBP2-Fc was added to each well and incubated 1 hour at room temperature followed by 5 washes of PBS. Goat-anti-human Ig Fc fragment specific (Jackson) was added and incubated for 1 hour followed by 5 washed with PBS. The plates were developed with TMB substrate (KPL) and read on a plate reader at 650 nm. Positive wells were subsequently screened against irrelevant Fc protein to remove antibodies reactive to human Fc. They were also screened by flow cytometry for binding to Con-A stimulated T cells and by immunoprecipitation of ULBP-2 transfected CV-1 cells. Positive hybridomas were cloned by titration and limiting dilution methods and grown in bulk culture. Supernatants were purified over a Protein A column (Bio-Rad) and stored at −20° C. Purified antibody was isotyped by ELISA capture assay (Mouse MonoAb-ID Kit, Zymed).

EXAMPLE 5

ULBP-mediated Enhancement of IFN-γ Production and NK Cell Proliferation

NK cells were generated after short term culture of peripheral blood lymphocytes as previously described (B. Perussia et al., *Nat. Immun. Cell Growth Rgulat.* 6:171–188, 1987). Further enrichment was obtained by negative selection with employment of the magnetic cell separator and magnetic beads (Miltenyi Biotec., Auburn, Calif.), according to the manufacturer's protocol. This procedure resulted in a population of >95% CD3−, CD16+, CD56+NK cells as assessed by FACS analysis performed after staining of the cells with the respective PE-conjugated monoclonal antibodies (Pharmingen).

Purified NK cells were stimulated with 50 ng/ml of IL-15 (Immunex Corp.) for 20 hours in RPMI1640 medium containing 10%FCS, supplemented with antibiotics and glutamnine, in a 37° C. humidified incubator with 5% $CO_2$, at a concentration of $2\times10^6$ cells/ml. After three washes with PBS, cells were cultured in RPMI1640 medium containing 10%FCS, supplemented with antibiotics and glutamine, in triplicate in a 96-well plate, at 100,000 cell/well in 250 μl volume, in the presence of rIL-12 (R&D Systems Inc., Minneapolis, Minn.) at a concentration of 1 ng/ml, alone or with ULBP1-LZ or ULBP2-LZ.

After 48 hours of culture, cell-free supernatants were analyzed for IFN-γ concentration using an IFN-γ specific ELISA, with employment of B133.1 monoclonal and P3'polyclonal anti-human IFN-γ antibodies. To evaluate cell proliferation, after 48 hours of culture, NK cells were pulsed for the last 16 hours with 30 μl of medium containing 40 μCi/ml of [methyl-$^3$H]Thymidine, harvested, and counted in a beta counter (Packard). These results demonstrate that the ULBPs are able to synergize with IL-12 in the production of IFNγ by NK cells and NK cell proliferation. IFNγ is essential for a TH1 immune response and it activates macrophages to kill tumor cells. It is also an antiviral cytokine.

EXAMPLE 6

ULBP-mediated Enhancement of CTL Activity

Peripheral blood mononuclear cells (PBMC) were isolated from heparinized blood by centrifugation over Ficoll-Hypaque and washed three times in culture medium (RPMI 1640 supplemented with 10% heat-inactivated fetal bovine serum, 50 U/ml penicillin, 50 μg/ml streptomycin and 2 mM glutamine). One million irradiated (3500 rads.) effector cells were cocultured with one million responder cells and ULBP1LZ or ULBP2LZ proteins. Cultures were conducted in a total volume of 2 mls culture medium at 37° C. in a humidified atmosphere of 5% $CO_2$ for 7 days. At this time, cultured cells were washed and put into a 4 hr chromium-release assay to assess cytolytic activity against $^{51}$Cr-labeled day 3 PHA blasts as described previously (M. R. Alderson, H. M. Sassenfeld and M. B. Widmer. *J. Exp. Med.* 172:577–587, 1990). Results are expressed as % specific $^{51}$Cr release from wells containing serially-diluted responder cells and a fixed number of labeled target cells.

EXAMPLE 7

ULBPs Bind to NKG2D

The following binding experiments demonstrate that the three ULBP proteins described herein bind to NKG2D, a -type lectin receptor found on NK cells, complexed with DAP10, a signal transducing adapter molecule. NKG2D expression is known to be enhanced by association with Dap10.

293E BNA cells were transfected separately with the pDC409 expression vector containing DNA encoding one of the following:

1. NKG2D+FLAG tagged Dap10
2. FLAG tagged Dap 10 alone
3. Empty pDC409 vector
4. Full length UL16 in pDC409 vector To detect the positive expression of NKG2D/Dap 10 on the cell surface an anti-FLAG antibody (M1 antibody) was used. M1 detects only cells expressing NKG2D+Dap10 and cells expressing Dap10 alone.

Standard binding experiments were carried out to determine if ULBP1, ULBP2, and ULBP3 bind to cells on which NKG2D is expressed. In addition to ULBP1, 2 and 3, a UL16 ligand, MICB/PERB11, and MICA, a MICB/PERB11 homologue known to bind NKG2D, were included in the binding experiments. Other constructs were also tested in the binding experiments and include P7.5/Fc, UL16/Fc, and hCD40Fc. Cells transfected with full length UL16 served as additional controls because UL16 is known to bind MICB, PERB11, ULBP1 and ULBP2. UL16 does not bind MICA or ULBP3. This confirms that the proteins that were identified as positively binding are binding appropriately and not non-specifically sticking to NKG2D/Dap10. The results are shown in Table I and confirm that all three ULBPs bind to NKG2D/Dap10. These results also suggest that NKG2D/Dap10 may be a receptor for the ULBP proteins.

TABLE I

| | Mean Fluorescence Intensity (MFI) - Transfected Protein | | | | |
|---|---|---|---|---|---|
| Staining Reagent | NKG2D/Dap10 | NKG2D | Dap10 | 409 Vector | UL16 FL |
| Sheep anti-mouse IgG PE (ShaM) | 9.17 | 8.28 | 12.03 | 11.84 | 10.6 |
| M1 (anti-FLAG + ShaM) | 130.47 | 8.49 | 111.9 | 12.31 | 11.34 |
| Goat anti-human IgG PE (GaH) | 9.4 | 8.71 | 12.79 | 11.47 | 10.54 |
| 2 μg MICA/FC + GaH | 120.48 | 15.43 | 11.99 | 17.83 | 13.99 |
| 2 μg MICB1/FC + GaH | 117.63 | 9.58 | 18.41 | 12.15 | 94.47 |
| 2 μg PERB11/FC + GaH | 109.4 | 10.16 | 12.72 | 12.86 | 161.42 |
| 2 μg ULBP1/FC + GaH | 115.07 | 10.41 | 13.62 | 15.42 | 141.85 |
| 2 μg ULBP2/FC + GaH | 116.66 | 8.96 | 11.46 | 12.02 | 121.41 |
| 2 μg ULBP3/FC + GaH | 101.6 | 9.55 | 13.96 | 14.11 | 11.95 |
| 2 μg p7.5/FC + GaH | 12.24 | 9.99 | 12.06 | 13.28 | 12.09 |
| 2 μg UL16/FC + GaH | 21.2 | 27.9 | 39.23 | 32.64 | 17.86 |
| 2 μg hCD40/FC + GaH | 13.26 | 10.72 | 15.58 | 14.06 | 11.46 |

EXAMPLE 8

ULBP Can Block Binding of Other Proteins to NKG2D/Dap10

The following demonstrates that a ULBP-1/LZ fusion protein can block binding of MICA/Fc, MICB/Fc, PERB11/Fc, ULBP-1/Fc, ULBP-2/Fc and ULBP-3/Fc to 293 E cells that are transfected with NKG2D/Dap10. The experiments were carried out by transfecting 293E cells with NKG2D/Dap10 and confirming expression of NKG2D/Dap10. Transfected 293E cells expressing NKG2D/Dap10 were preincubated with excess of ULBP-1/LZ before exposing the 293 cells to MICA/Fc, MICB/Fc, PERB11/Fc, ULBP-1/Fc, ULBP-2/Fc or ULBP-3/Fc. Table II details the results of this blocking experiment. The results demonstrate that ULBP-1, MICA, MICA, PERB11, ULBP-2 and ULBP-3 bind to the same or overlapping sites on NKG2D/DAP10.

TABLE II

| BLOCKING PROTEIN Values Given In Mean Fluorescence Intensity (MFI) | | |
|---|---|---|
| | 25 μg ULBP1/LZ | 25 μg hCD40L/LZ |
| 2 μg MICA/FC + GaH | 11 | 256 |
| 2 μg MICB/FC + GaH | 9 | 258 |
| 2 μg PERB11/FC + GaH | 11 | 280 |

TABLE II-continued

| | | |
|---|---|---|
| 2 μg ULBP1/FC + GaH | 11 | 263 |
| 2 μg ULBP2/FC + GaH | 8 | 236 |
| 2 μg ULBP3/FC + GaH | 13 | 267 |
| 2 μg UL16/FC + GaH | 19 | 32 |
| 2 μg hCD40/FC + GaH | 12 | 35 |

| Controls: | MFI |
|---|---|
| Goat anti-human IgGPE | 6 |
| Sheep anti-mouse IgGPE | 5 |
| M1 (anti-FLAG) + ShaM | 368 |

EXAMPLE 9

ULBP Antibodies Block Binding to NKG2D/Dap10

The following demonstrates the ability of certain anti-ULBP antibodies and PERB11 antibodies to block binding of binding protein, to which the antibody is specific, to NKG2D/Dap10. The antibodies used included anti-ULBP-1, anti-ULBP-2, anti-ULBP-3, and anti PERB11, all prepared as described above. The binding experiments were carried out using conventional binding techniques. Prior to adding the binding protein to 293E cells transfected with NKG2D/Dap 10, the binding proteins were preincubated with excess amounts of the antibody to which they are specific. As shown in Table III, anti-ULBP-1 antibodies, M291 and M295 block ULBP-1/Fc from binding to NKG2D/Dap10. But antibody M90, (an isotype matched control antibody) does not block binding. Anti-ULBP-1 antibodies, M292, M293 and M294 do not block ULBP-1 binding to NKG2D/Dap10. Anti-ULBP-2 antibody M311 blocks ULBP2/Fc binding to NKG2D/Dap10, but M310, M312 and M90 do not block the binding. Anti-ULBP-3 antibody 550 does not block ULBP3/Fc binding to NKG2D/Dap 10. Finally, anti-PERB11 antibody M360 blocks PERB11 binding to NKG2D/Dap10, but anti-PER11 antibodies M361 and M362 do not block binding. These results confirm specificity of the antibodies tested.

TABLE III

Staining Protein + Goat anti-huIgGPE
Values Given in Mean Fluorescence Intensity (MFI)

| Blocking Antibody | ULBP1/FC | ULBP2/FC | ULBP3/FC | PERB11/FC |
|---|---|---|---|---|
| M291 | 8 | | | |
| M292 | 179 | | | |
| M293 | 220 | | | |
| M294 | 187 | | | |
| M295 | 18 | | | |
| M90 (Isotype Matched) | 216 | | | |
| M310 | | 107 | | |
| M311 | | 60 | | |
| M312 | | 160 | | |
| M90 | | 192 | | |
| M550 | | | 165 | |
| M90 | | | 160 | |
| M360 | | | | 8 |
| M361 | | | | 179 |
| M362 | | | | 170 |
| M90 | | | | 167 |

| Controls: | MFI |
|---|---|
| Goat anti-human IgGPE alone | 6 |
| Sheep anti-Mouse IgGPE alone | 4 |
| M1 (anti-FLAG) + ShaM | 261 |

What is claimed is:

1. An isolated polypeptide comprising an amino acid sequence that is at least 80% identical to amino acids 20 to 200 of SEQ ID NO:2, wherein the polypeptide binds cells expressing NKG2D and Dap10.

2. The polypeptide of claim 1 comprising an amino acid sequence that is at least 90% identical to amino acids 20 to 200 of SEQ ID NO:2.

3. The polypeptide of claim 1 comprising amino acids 20 to 200 of SEQ ID NO:2.

4. The polypeptide of claim 1 comprising amino acids 22 to 219 of SEQ ID NO:2.

5. The polypeptide of claim 1 comprising amino acids 30–117 of SEQ ID NO:2.

6. The polypeptide of claim 1 comprising amino acids 118–200 of SEQ ID NO:2.

7. The polypeptide of claim 1 conjugated to another protein or polypeptide.

8. The polypeptide of claim 7 wherein the polypeptide is an Fc polypeptide.

9. The polypeptide of claim 1 conjugated to a diagnostic or therapeutic agent.

10. The polypeptide of claim 1 that is glycosylated.

11. The polypeptide of claim 1 that is soluble.

12. An isolated polypeptide comprising amino acids x through y of SEQ ID NO:2, wherein x is an integer selected from the group consisting of 20 through 3,0, inclusive, and y is an integer selected from the group consisting of 200 through 227, inclusive, of SEQ ID NO:2.

13. The polypeptide of claim 12 conjugated to another protein or polypeptide.

14. The polypeptide of claim 13 wherein the polypeptide is an Fc polypeptide.

15. The polypeptide of claim 12 conjugated to a diagnostic or therapeutic agent.

16. The polypeptide of claim 12 that is glycosylated.

17. The polypeptide of claim 12 that is soluble.

18. An isolated polypeptide encoded by a polynucleotide, wherein the polynucleotide or its complement hybridizes to the DNA of SEQ ID NO:1, wherein the hybridizing conditions include 50% formamide and 6×SSC, at 42 degrees C with washing conditions of 60 degrees C., 0.5×SSC, 0. 1% SDS, and wherein the polynucleotide encodes a polypeptide that binds cells expressing NKG2D and Dap10.

19. The polypeptide of claim 18 conjugated to another protein or polypeptide.

20. The polypeptide of claim 19 wherein the polypeptide is an Fc polypeptide.

21. The polypeptide of claim 19, wherein the polypeptide has the sequence of SEQ ID NO:7.

22. The polypeptide of claim 18 conjugated to a diagnostic or therapeutic agent.

23. The polypeptide of claim 18 that is glycosylated.

24. The polypeptide of claim 18 that is soluble.

25. A method for producing an antibody comprising using the polypeptide of claim 17 as an immunogen to generate an antibody that binds to the polypeptide of claim 18.

26. A method for assaying binding of the polypeptide of claim 18 to NKG2D and Dap10 comprising contacting the polypeptide with NKG2D and Dap10, and detecting binding of the polypeptide to NKG2D and Dap10.

27. The method of claim 26, wherein the polypeptide is further contacted with an inhibitor.

28. The method of claim 27, wherein the inhibitor is a protein.

29. A method for producing an antibody comprising using the polypeptide of claim 19 as an immunogen to generate an antibody that binds to the polypeptide of claim 1.

30. A method for assaying binding of the polypeptide of claim 1 to NKG2D and Dap10 comprising contacting the polypeptide with NKG2D and Dap10, and detecting binding of the polypeptide to NKG2D and Dap10.

31. The method of claim 30, wherein the polypeptide is further contacted with an inhibitor.

32. The method of claim 31, wherein the inhibitor is a protein.

* * * * *